US005663484A

United States Patent [19]
Sarreal et al.

[11] Patent Number: 5,663,484
[45] Date of Patent: Sep. 2, 1997

[54] BASMATI RICE LINES AND GRAINS

[75] Inventors: Eugenio S. Sarreal, Pearland; John A. Mann, Friendswood; James Edward Stroike, League City; Robin D. Andrews, Seabrook, all of Tex.

[73] Assignee: RiceTec, Inc., Alvin, Tex.

[21] Appl. No.: 272,353

[22] Filed: Jul. 8, 1994

[51] Int. Cl.$^6$ .............................. A01H 5/00; A01H 5/10; A01H 1/04

[52] U.S. Cl. ................. 800/200; 800/205; 800/DIG. 57; 47/58; 47/DIG. 1

[58] Field of Search ................................. 800/200, 250, 800/DIG. 57; 47/58, 58.01, 58.03, DIG. 1

[56] References Cited

U.S. PATENT DOCUMENTS 5,208,063  5/1993  Andrews et al. ........................ 426/482

OTHER PUBLICATIONS

Bollich, C. N. Am. J. Bot. Annual Meeting Botanical Society of America. 79(6 Suppl.):88. Jan. 1992.
Allard, R. W. In Principles of Plant Breeding. John Wiley & Sons, Inc. New York. New York. pp.: 67–72. Jan. 1960.
Rasper, V., "Theoretical Aspects of Amylographology" in *The Amylograph Handbook*, Shuey and Tipples, American Association of Cereal Chemists, Chapter 1, pp. 1–15.
Flour Milling and Baking Research Association Annual Report of Rice Quality and Rice Authenticity, 1993.
Juliano, B., 1985, *Cereal Foods World* 30:651–656.
Juliano, B., "Amylose Analysis in Rice—A Review" in *Chemical Aspects of Rice Grain Quality*, International Rice Institute, 1979, pp. 251–260.
Sagar et al., 1988, *Journal of Agricultural Research* Oct.–Dec. pp. 16–21.
Juliano, B., "Polysaccharides, Proteins, and Lipids of Rice" in *Rice: Chemistry and Technology*, Cereal Chemistry Dept. International Rice Research Institute, 1985, pp. 59–85.
Osborne et al., 1993, *J. Near Infrared Spectroscopy* 1:77–83.
Correspondence from Agriculture Counselor—New Delhi USDA/FAS to USA Rice Council, Dec. 1993.
Shobha Rani, N., Paper on "Research Efforts to Develop Scented Quality Rices", International Rice Research Conference, Apr. 1992.
Sood and Siddiq, 1980, *Z. Pflanzenzuchtg* 84:294–301.
Rao, M., 1989, *International Rice Research Newsletter* 14:10–11.
Berner and Hoff, 1986, *Crop Science* 26:876–878.
Yanjun et al., 1992, *International Rice Research Newsletter* 17:2.
Briggs and Knowles, 1967, "Breeding Self-Pollinated Crops by Hybridization and Pedigree Selection", in *Introduction to Plant Breeding* Chapter 11, pp. 133–146.
Briggs and Knowles, 1967, "Bulk Population Methods of Breeding Self-Pollinated Plants" in *Introduction to Plant Breeding* Chapter 12, pp. 147–161.
Briggs and Knowles, 1967, "The Backcross Method of Breeding", in *Introduction to Plant Breeding* Chapter 13, pp. 162–173.
Allard, R.W., 1966, "Pure–Line Breeding and Mass Selection" in *Principles of Plant Breeding* Chapter 11, pp. 109–114.
Allard, R.W., 1966, "Pedigree Method of Plant Breeding" in *Principles of Plant Breeding* Chapter 12, pp. 115–128.
Allard, R.W., 1966, "Bulk–Population Breeding" in *Principles of Plant Breeding* Chapter 13, pp. 129–149.
Allard, R.W., 1966, "Backcross Breeding" in *Principles of Plant Breeding* Chapter 14, pp. 150–165.

*Primary Examiner*—David T. Fox
*Assistant Examiner*—Melissa L. Kimball
*Attorney, Agent, or Firm*—Pennie & Edmonds LLP

[57] ABSTRACT

The invention relates to novel rice lines and to plants and grains of these lines and to a method for breeding these lines. The invention also relates to a novel means for determining the cooking and starch properties of rice grains and its use in identifying desirable rice lines. Specifically, one aspect of the invention relates to novel rice lines whose plants are semi-dwarf in stature, substantially photoperiod insensitive and high yielding, and produce rice grains having characteristics similar or superior to those of good quality basmati rice. Another aspect of the invention relates to novel rice grains produced from novel rice lines. The invention provides a method for breeding these novel lines. A third aspect of the invention relates to the finding that the "starch index" (SI) of a rice grain can predict the grain's cooking and starch properties, to a method based thereon for identifying grains that can be cooked to the firmness of traditional basmati rice preparations, and to the use of this method in selecting desirable segregants in rice breeding programs.

20 Claims, 10 Drawing Sheets

FIG. 1A RATING 2

FIG. 1C RATING 3

FIG. 1E RATING 4

FIG. 1G RATING 5

FIG. 1H RATING 6

FIG. 1J RATING 7

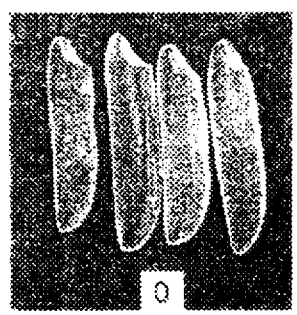 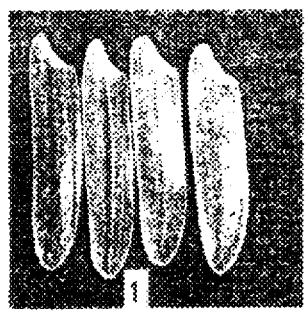 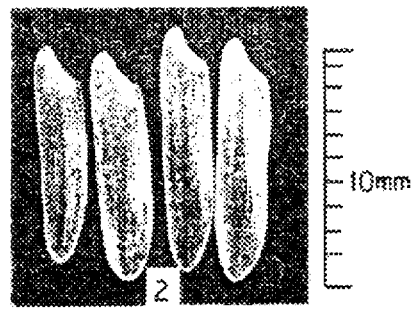
FIG.2A FIG.2B FIG.2C
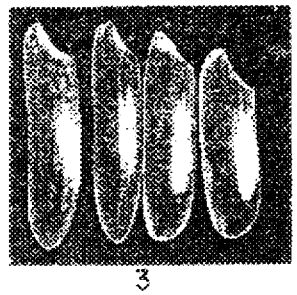 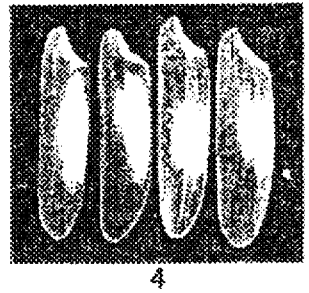 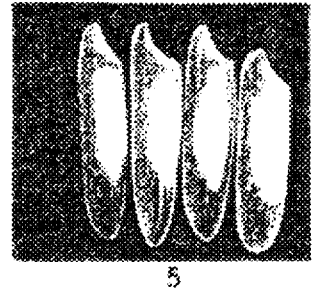
FIG.2D FIG.2E FIG.2F

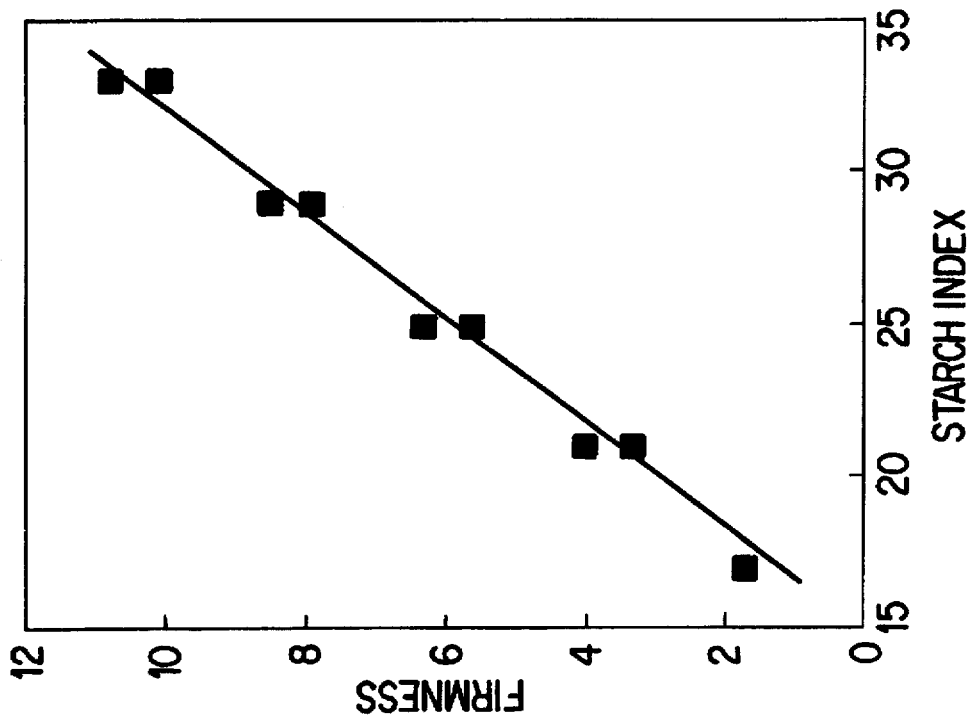
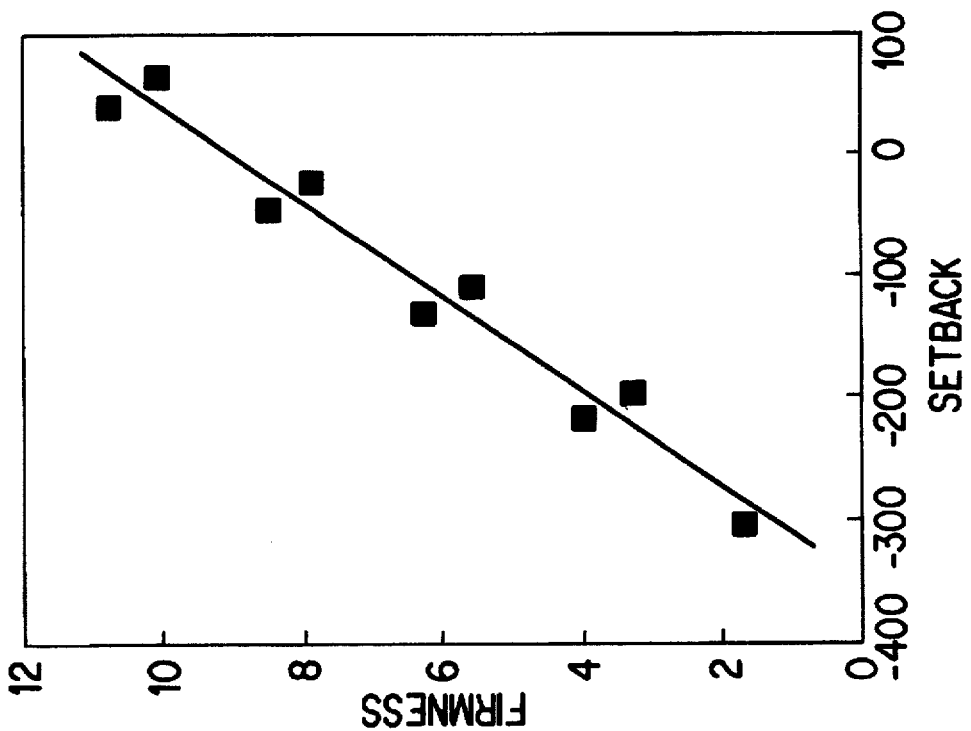
FIG. 6 B
FIG. 6A

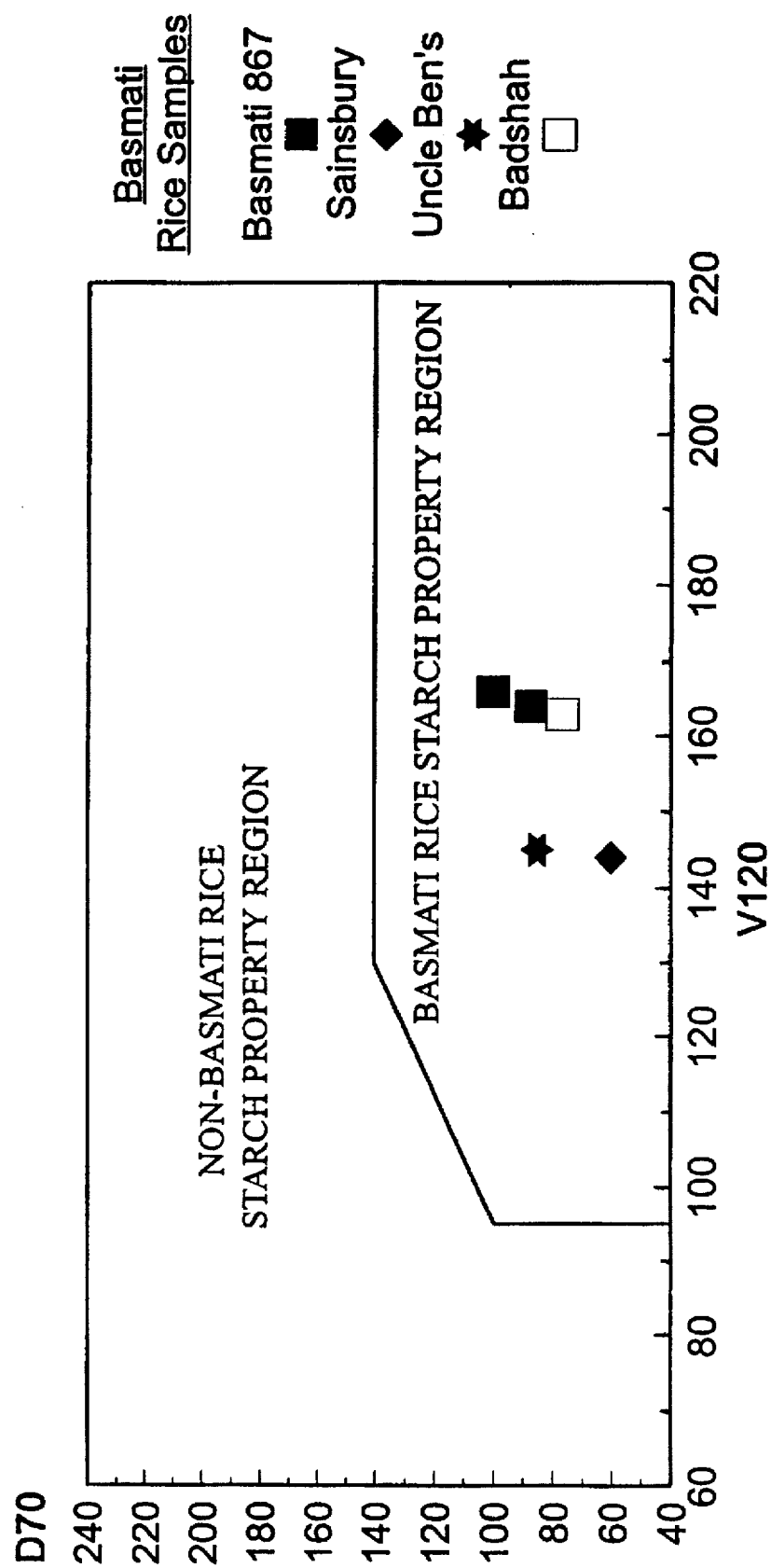

BASMATI RICE LINES AND GRAINS

1. FIELD OF INVENTION

The invention relates to novel rice lines and to plants and grains of said lines. The invention also relates to a novel method for identifying rice grains that can be cooked to a specific texture and the use of said method to select for desirable rice plants in breeding programs. Specifically, one aspect of the invention relates to novel rice lines with plants that are semi-dwarf in stature, substantially photoperiod insensitive and high yielding, and that produce rice grains having characteristics similar or superior to those of good quality basmati rice grains produced in India and Pakistan. Another aspect of the invention relates to novel rice grains produced from said novel rice lines. The third aspect of the invention relates to the finding that the likely texture and firmness of cooked rice can be predicted by the "starch index" (SI) of the grain and to the use of SI to identify desirable segregants in rice breeding programs.

2. INTRODUCTION

2.1. Cooking Behavior and Starch Properties of Rice

The cooking behavior and the texture of cooked rice are dependent on the starch properties of the uncooked rice, particularly the percentage amylose. The presence of lipids effects the measurement of percentage amylose. Apparent amylose (i.e., lipids not removed by solvent extraction) is the usual measurement (1979, Proceedings of the Workshop on Chemical Aspects of Grain Quality, International Rice Research Institute (IRRI). High amylose rice requires a higher water/rice ratio, for cooking to a given firmness, than low amylose rice. The gelatinization temperature (GT) is also considered important and is often measured indirectly by rating the Alkali Spreading Value (ASV) of milled rice grains digested for a time in a dilute solution of potassium hydroxide (KOH). Grain dimensions also effect cooking time with finer grains cooking faster. A property known as gel consistency is also measured as a means of differentiating between rice types. Gel consistency measures the tendency of cooked rice to harden on cooling. Gel consistency typically is classified as hard, medium and soft. For a treatise on the physicochemical properties of rice see, *Rice Chemistry and Technology*, 1985, B. O. Juliano, ed., American Assoc. Cereal Chem. Inc., St. Paul, Minn.

The milling process affects the cooking behavior of rice grains. Rice which is milled to remove the bran but leave more of the aleurone and sub-aleurone layers in place cooks drier and fluffier than rice which has been milled to a much higher degree. See U.S. Pat. No. 5,208,063, May 4, 1993, Milling Process for Controlling Rice Cooking Characteristics.

Starch properties and rice cooking behavior are assessed directly by cooking the grains in controlled tests and also by using an amylograph in which the viscosity profile of a rice paste is measured as it is heated, cooked and cooled using a time-temperature program. The gelatinization temperature, the peak viscosity, the hot paste viscosity, and the cool paste viscosity are measured. The amylograph profile and these values are useful for characterizing varietal differences, measuring variations within a variety, and studying the effect of growing environment on the starch and cooking properties. Amylograph data is related to other starch property measurements such as percentage amylose and gel consistency. However, amylograph paste viscosity is impacted by the presence of lipids in rice, changes in the composition of the lipids with aging of the grain, and the manner in which the test is conducted.

Grain from the seed of a rice variety grown in one environment may have different starch properties when grown in a different environment. Temperature during grain ripening, for example, is known to affect amylose content and ASV with cooler temperatures tending to increase both values. Amylograph profile and grain cooking behavior may differ when the variety is grown in different environments.

2.2 Basmati Rice

Although there is no single precise definition of basmati rice, it is generally accepted that good quality basmati rice has a unique combination of characteristics. Good quality basmati rice has a distinctive and pleasant aroma, long slender grains, extreme grain elongation on cooking, and a dry, fluffy texture when cooked. See Sood and Siddiq, 1980, Studies on Component Quality Attributes of Basmati Rice, *Oryza Sativa*, L.; Z. Pflanzenzuchtg 84:294–301. The distinctive aroma of basmati rice has been described as "popcorn" like and identified as being mostly due to the presence of 2-acetyl-1-pyrroline (2-AP). Good basmati rice typically has an average milled length to width ratio of around 4 and elongates lengthwise about 100% or so when cooked. Basmati rice which can be cooked to a dry and fluffy texture is traditionally preferred and a premium is paid for this quality.

Some basmati rice is parboiled. Parboiled basmati rice is called Sella Basmati in India and the Middle East, and Easy Cook Basmati in the United Kingdom. Parboiling results in a yellowed rice with clear translucent grains. The characteristic chalkiness and aroma of basmati rice are eliminated in the parboiling process. Parboiled basmati grains elongate little more than regular rice during cooking. The uncooked and cooked grains of parboiled basmati rice are somewhat narrower than most long grain rice. Parboiled basmati rice has improved vitamin content (more thiamine and nicotinic acid) and fewer grains break during the milling process. The parboiled basmati rice requires a higher water/rice ratio than regular basmati rice, takes longer to cook, and the cooked grains are beady rather than fluffy in appearance. The cooking of parboiled basmati rice is perceived to be more forgiving and produces separate grains over a wider range of cooking conditions than regular basmati rice.

2.3 Indian and Pakistan Basmati Rice

Good quality basmati rice traditionally has come from northern India and Pakistan. Some of the better known good quality basmati varieties from India and Pakistan include Basmati 370, Type-3 (Dehradum Basmati) and Karnal Local. The superior quality of such basmati rice is well known to discriminating rice consumers. Indeed, in some countries the term "basmati rice" can be applied to only the basmati rice grown in India and Pakistan. For example, the Grain and Feed Trade Association in the United Kingdom (the largest basmati rice market in Europe and one of the largest importers of basmati rice in the world) in cooperation with the U.K. Local Authorities Coordinating Body on Trading Standards (LACOTS) has established a *Code of Practice for Rice* which is used by companies which operate in that market. This code allows the term basmati rice to be applied to only the long grain aromatic rice grown in India and Pakistan. Similarly, Saudi Arabia, the world's largest importer of basmati rice, has labeling regulations that permits basmati rice from only India and Pakistan and not Thailand to be marketed as basmati rice.

The basis of the distinctiveness of good quality Indian and Pakistan basmati rice remains unclear. Some believe that it is due to a unique combination of the particular plant varieties cultivated, the climatic and soil conditions and the cultivation practices indigenous to northern India and Pakistan. See Fantastic Foods® Basmati Rice Package, United States, 1994; Tilda® Basmati Rice Package, United States, 1994. In northern India and Pakistan, basmati seed are planted in nursery beds during July. In August and September, when the seedlings reach about eight inches in height, they are transplanted by hand in water flooded fields. The rice is harvested towards the end of October and in November. The plants are tall in stature (about 160 cm or more) and prone to lodging. Only modest mounts of fertilizer are used. Field yields are low at about 2,000 to 2,500 lbs per acre but the crop is economically viable since basmati rice from these regions sells in world markets for about twice the price of regular rice.

Notwithstanding the high demand for good quality Indian and Pakistan basmati rice, grain chalkiness is a notable deficiency of nearly all Indian and Pakistan basmati rice. Consumers generally prefer translucent or creamy white grains over dull, chalky grains. Chalk-like appearance on the dorsal side of the grain is known as "white belly" and in the center of the grain as "white center". Basmati rice from India and Pakistan has a higher percentage of white centered and white belly grains than American long grain rice. This apparently is varietal and environmentally related. The harvesting of basmati rice late in the year in India and Pakistan under wet and cool conditions can increase chalkiness. Aside from inferior visual appeal, chalky grains tend to break during milling. This causes an economic loss since broken grains are of a lower value. Broken grains are not desirable in basmati rice for reasons of appearance and causing stickiness in the cooked rice. Moreover, even where the grains remain intact, chalky grains tend to be soft and discolored when cooked, which is undesirable in basmati rice preparations.

Measurements of perceived good quality basmati rice from India and Pakistan show in general that the grains: (i) elongate by more than 75% during cooking, yielding whole grains with a length to width ratio >3.5, (ii) have a strong "popcorn" aroma, (iii) are somewhat chalky (white center) and generally have a low transparency, (iv) are often milled to a low degree and thus show more bran streaks, (v) vary considerably in color and chalkiness from lot to lot, and (vi) cook to a dry and fluffy texture. Good quality basmati rice from India and Pakistan also have distinctive starch properties in the way of apparent amylose contents of greater than 21%, low gelatinization temperatures and a medium to hard gel consistency.

The variable quality of Indian and Pakistani basmati rice has compelled many commercial buyers of such rice to take extensive quality assurance measures. Experienced buyers examine the paddy or brown rice, test mill the rice, examine milled rice quality; and cook a white milled rice sample before making an overall assessment of value and price. The number of attributes to be assessed in basmati rice is greater than for any other rice product, the potential for error is significant, and the high cost of the rice increases the financial risk to a prospective purchaser. The common practice of storing or aging basmati rice for many months creates an opportunity for insect infestation, discoloration and a loss of identity as lots are often mixed together. It is allowable in the UK for basmati rice from these countries to contain a 10% admixture of other varieties and this complicates evaluations. Many rice purchasing/marketing companies require strict control of quality throughout the production chain, including knowledge of the specific variety and the use of pesticides and chemicals during production and storage. This is difficult and often impossible to determine when the rice is grown remotely from the market in the West. Importation of basmati rice into the United States has been stopped on occasions by the federal grain inspection authorities due to significant infestation and contamination problems.

2.4. Basmati Rice Production Elsewhere

Seeds of the traditional basmati rice varieties have been produced outside of India and Pakistan but not on a commercial basis. Most of these varieties are photoperiod sensitive and require a specific, short day length before they will flower. This results in the plants flowering and maturing in the fall of the year regardless of the date of planting. Such photoperiod sensitive basmati rice grown at about the same latitude in another country (e.g., about 30° N in Texas in the United States) will be ready for harvest in late October or November, which is too late for a commercial crop. If planted in March (a normal planting time in Texas) the plant will add foliage until the critical day length is reached and will only then flower. Consequently, the plants become very tall and leafy, causing lodging under high winds and rainy conditions. The maturity of such Texas-grown basmati varieties can reach 200 days or more. In contrast, a typical U.S. rice variety matures and can be harvested in about 115 days after seeding and a ratoon crop may also be obtained after another 45 days. Late June or July planting of a photoperiod sensitive Indian or Pakistan basmati line gives a better plant type but the yields are low and the rice may be subject to early frosts and may not mature.

2.5. Basmati Rice Breeding Efforts

Efforts to improve the versatility or productivity of basmati rice lines have had only limited success. One prong of such efforts has been to breed rice lines that can be productively cultivated in the Western hemisphere and produce grains with some of the desired basmati grain characteristics. These efforts have yielded a number of aromatic rice types often referred to generically as "basmati type rice", including Della rice and the widely distributed Texmati® brand rice. These products have somewhat less aroma and flavor than premium basmati rice from India and Pakistan. Moreover, they typically elongate only 50% on cooking (which is about the same extent as regular long grain rice), and have cooked textures somewhat different than that of traditional good quality basmati rice.

Another prong in the improvement effort has been that of the Indian and Pakistani scientists, which is to breed higher yielding, more widely adapted basmati varieties. Their objective has been to reduce costs and to expand basmati production into other parts of the Indian subcontinent. These efforts were started in the mid-sixties with the objective of transferring the unique quality grain features of traditional basmati rice into the high yielding semi-dwarf "Green Revolution Rice Types" varieties. Such transfers are desirable in part as photoperiodism has been bred out of most of the semi-dwarf varieties. In general, the days from planting to maturity of a non-photoperiod sensitive plant do not differ much when planted at different times of the year. Thus, such plants are more adaptable to different growing regions and conditions than are photoperiod sensitive plants. Achieving this in basmati whilst maintaining all of the desired grain traits has not been accomplished. Despite decades of persistent effort, the targeted genotypes have not been achieved.

Although nearly a score of new varieties have been released between 1970 and 1992 which possessed medium slender to long slender grains with aroma, none has all of the quality traits of traditional basmati. More recently, new semi-dwarf (about 105 cm tall) basmati varieties Kasturi and Pusa Basmati-1 have been released (N. Shoba Rani, 1992, Research Efforts to Develop Scented Quality Rice—India—IRRI Newsletter). These are more promising but again they do not have all the properties of traditional basmati (Letter from Agriculture Counselor-New Delhi USDA/FAS to USA Rice Council-December 1993). Thus, even though some call the new varieties basmati rice, the new varieties more properly should be described as basmati substitute or quasi basmati rice.

The limited success in improving the versatility and productivity of basmati rice lines supports the belief in consumer, trade and scientific circles that authentic basmati rice can only be obtained from the northern regions of India and Pakistan due to the unique and complex combination of environment, soil, climate, sowing practices and the genetics of the basmati varieties. For example, a typical basmati rice package states: "Basmati rice has been grown for centuries near the foothills of the Himalayas in northern India where the soil conditions are optimal. Farmers in other parts of the world have attempted to duplicate Basmati Rice but have not been able to capture the unique qualities of the original, authentic Indian variety" (Fantastic Foods® Basmati Rice Package—United States—1994). Another package states "Tilda® Basmati rice has traveled from the foothills of the Himalayas. It has been carefully tended and harvested by hand in an area whose unique soil and climatic characteristics give the rice its exquisitely delicate texture, flavor, and aroma" (Tilda® Basmati Rice Package—United States—1994).

Scientifically, it has been reasoned that the cool growing temperatures and the late harvesting of basmati rice prevalent in northern India and Pakistan account for the low gelatinization temperature and perhaps the high chalkiness of authentic basmati rice and that these properties are essential to the particular basmati cooked grain characteristics. It has also been reasoned that these cool conditions are responsible for the high level of aroma and flavor associated with the presence of 2-acetyl-1-pyrroline since this compound is volatile. On this basis then it would not be possible to achieve the desirable basmati grain properties and qualities by breeding them into a semi-dwarf plant which would mature quickly and grow in a hotter climate, even if the complex trait breeding process could be accomplished. See Soomo and McLean, 1992, High Yielding Rice Varieties in West Pakistan, International Rice Research Institute.

2.6. Breeding Challenges

Speculations aside, the challenges in developing higher yielding, widely adapted and higher quality basmati varieties are formidable. The odds against the successful combining of basmati grain traits with desirable plant traits found in advanced semi-dwarf varieties by plant breeding is daunting. Basmati grains have four to five characteristic traits, i.e., aroma, elongated grain shape (grain length and width), extreme elongation of the cooked grain and dry, fluffy cooked texture. Of these, aroma is perhaps the most simply inherited. Most literature suggests either one or two genes (and possibly an additional repressor gene) as encoding the functions giving rise to aroma. (Berner and Hoff, 1986, Inheritance of Scent in American Long Grain Rice, Crop Science 26:876–878; Dong et al., 1992, Genetic studies of aroma in the elite cytoplasmic male sterile (CMS) aromatic japonica line, Shanghai A, International Rice Research Institute Newsletter 17:5). The quantitative aspect of aroma, however, has not been described, but may well be controlled by several more genes. The genetics of the other basmati grain traits is even less well understood. However, each of these other traits is likely encoded by more genes than those determining aroma. Even assuming an average of only 7 genes in encoding each of the other three basmati grain traits, then the ideal combination of all basmati-specific grain traits will occur with a frequency of less than 1:900. In comparison, it is often assumed that at least one hundred genes are involved in the quantitative aspects of agronomically important plant traits such as seed yield, milling yield, plant height, maturity, tillering, panicle shape and size, disease resistance and photoperiod sensitivity. Together, the frequency of the "best combination" of desirable basmati grain and semi-dwarf plant traits is likely to be less than 1:16,000.

Moreover, many of these grain and plant traits are highly responsive to the environment. For example, milling yields might vary from 20% to 65%, grain starch properties, which control rice cooking behavior and cooked rice texture, might also vary widely, and yield can vary from nil to 10,000 kilograms/hectare, all depending on the environment. This highly complicates the chances of finding the 1 variant in 16,000. Moreover, as the genes encoding these traits do not assort at random, the odds are further diminished. For example, in basmati rice good grain traits appear to be strongly associated with poor plant types. Such unfavorable linkages further diminish the odds of success. Thus, it is unclear that, even under favorable circumstances, classical plant breeding can produce a rice plant that combine desirable basmati grain traits with the superior plant traits of semi-dwarf rice varieties.

The difficulties in breeding higher yielding, widely adapted and higher quality basmati varieties is further compounded by the fact that the desirable dry, fluffy cooked texture of good quality basmati rice is a complicated trait and a difficult one to assay. Although the trait is genetically determined, its manifestation in cooked rice is controlled by the way the rice is processed and cooked. Rice which is milled to remove the bran but leave more of the aleurone and sub-aleurone layers in place cooks drier and fluffier than rice which has been milled to a higher degree. See Osborne et al., 1993, The Authentication of Basmati Rice Using Near Infrared Spectroscopy, Near Infrared Spectroscopy 1:77–83; Flour Milling and Baking Research Association (FMBRA) report for United Kingdom (UK) Ministry of Agriculture and Fisheries year ending March 1993. Aging of the rice, for months or years, also enhances this trait. The extent of milling and aging, however, also changes the way the rice cooks. Specifically, both aging and reduced milling increases the amount of water and the time needed to cook the rice to the desired optimal texture. Thus, assaying this trait in cooked rice must consider the interplay of these different factors and the results obtained therefrom must be interpreted accordingly.

The texture of the cooked rice may be directly assayed by eating the cooked rice or mechanically measuring its firmness. The cooked texture trait of rice can also be indirectly assessed by examining its cooking behavior and starch properties. Both of which can be quantitatively evaluated by amylography, which continuously measures and records the viscosity of a rice paste as it is heated, cooked and cooled according to a time-temperature program. The recorded amylograph profile allows for the determination of the gelatinization temperature, peak viscosity, hot paste viscosity, and cool paste viscosity. The interpretation of the amylographs of flours is well known (see *The Amylograph Handbook*, American Association of Cereal Chemists, 1988) and many studies have been conducted on different types of rice (see *Chemical Aspects of Grain Quality*, IRRI 1979; *Rice Chemistry and Technology*, Juliano, ed., American Association of Cereal Chemists). A study by FMBRA in the UK examined the amylographs of basmati rice and defined the likely shape of amylograph curves for basmati and non basmati types (*The Authentication of Basmati Rice Using Near Infrared Transmittance Spectroscopy*, FMBRA, March 1993). Basmati rice starch properties, without amylographs, have been reported by Sagar et at. (Grain Quality Characteristics of Pakistani Commercial Rice Varieties, Journal of Agricultural Research, October–December 1988, pages 16–21). A general understanding of the relationship between cooking behavior and starch properties is therefore available although the specific requirements and property ranges for a basmati rice of a preferred quality remains unclear. Additionally the large sample requirements for conducting a battery of tests (i.e., amylose, ASV, gel consistency, amylography, cooked rice firmness and fluffiness) preclude the comprehensive screening of cooking behavior in the early stages of a breeding program. Moreover, the assays themselves are cumbersome to conduct, requiring lengthy procedures and/or specialized equipment or experts. Thus, it has been difficult to effectively select and breed for the texture trait early in rice breeding programs.

3. SUMMARY OF THE INVENTION

One aspect of the instant invention relates to novel rice lines and to the plants and grains of said lines. Another aspect of the invention provides for a novel method of identifying rice grains that can be cooked to the dry and fluffy texture typically found in good quality basmati rice preparations and the use of said method to select desired lines in rice breeding programs. In particular, the present invention provides novel rice lines, whose plants are semi-dwarf in stature, substantially photoperiod insensitive, high yielding and produce rice grains comprising grain characteristics and qualities similar or superior to those of good quality basmati rice grains produced in India and Pakistan. The invention also relates to the discovery that the likely texture of cooked rice can be predicted by measuring a grain's "starch index" (SI), which is the sum of its percent amylose (PA) and alkali spreading value (ASV), and the use of SI in selecting desirable segregants in rice breeding programs.

The present invention makes possible the production of high quality, higher yielding, basmati rice worldwide. It is based, among other things, on the surprising discovery that certain basmati plant and grain characteristics and aspects of the growing environment for traditional basmati rice lines are not critical to perceived basmati product quality and that classical plant breeding methods can be used to combine, in novel rice lines, the desirable grain traits of basmati varieties with the desirable plant and grain traits of semi-dwarf, long grain varieties. The invention is also based, in part, on the discovery that the texture of cooked grains is related to the uncooked grains' SI. Seeds exhibiting a PA or ASV which might previously be rejected on a separate basis are found to give acceptable rice cooking behavior and texture when the SI lies within certain limits. In this way the effectiveness of the breeding process is improved. The SI can be easily and conveniently determined with a very small amount of sample, the discovery enables effective selection and thus breeding of the texture trait that heretofore has been an obstacle in the breeding of basmati grain traits. The invention is illustrated by several examples of novel rice lines whose plants embodies the desired combination of plant and grain traits. These new lines evidence the reproducibility and broad applicability of the disclosed teachings in developing the claimed novel rice lines.

3.1. Definitions

In order to provide a clear and consistent understanding of the specification and claims, including the scope to be given to a term, the following definitions are given to various terms used herein.

| | |
|---|---|
| ADAPTATION | The ability of plants to perform well in varying environmental conditions. |
| ASV | Alkali Spreading Value. |
| BAS 867 | Same as Basmati 867, Basmati 17867. |
| BURSTING INDEX | Index of intactness of cooked grains. |
| CHALKINDEX | The percent of grains with white centers or white bellies; or 100 X the probability that a particular grain will have a white center or white belly. |
| COOL | When used in the Tables or Figures, Cool is an abbreviation of the Cool Paste Viscosity. |
| GRAIN | The term is used herein to mean milled grain. |
| HEAD MILLED RICE | Whole grain rice. |
| HOT | When used in the Tables or Figures, Hot is an abbreviation of the Hot Paste Viscosity. |
| MATURITY | The time between planting and harvesting. Typically, maturity is equal to the days to flowering plus 20 to 30 days. |
| PA | Percent Amylose. The PA values reported herein pertain to "apparent" amylose, which is measured without existing lipids from the sample. |
| PEAK | When used in the Tables or Figures, Peak is an abbreviation of the Peak Viscosity. |
| RICE GRAIN | Same as grain (i.e., milled grain). |
| RVA | Rapid Visco Analyser. An instrument developed by Newport Scientific, Ltd. used to detemine the viscosity of a sample at different temperatures. |
| SMD | Satake Milling Degree. The degree of grain milling as determined by a Satake Milling Degree Meter. |
| SEED | The term is used herein to describe a rough rice grain (i.e., not |

| | |
|---|---|
| | dehulled). |
| SETBACK | Peak Viscosity subtracted from the Cool Paste Viscosity. |
| STARCH INDEX | The sum of PA and ASV. |
| SUBSTANTIALLY PHOTOPERIOD INSENSITIVE | The term describes a plant, whose flowering is predominately controlled by plant age. Such a plant can flower under a wide range of day lengths, once the critical age is reached. This contrasts with a photoperiod sensitive plant, whose flowering is triggered by a specific day length. |
| WHOLE GRAIN | A milled grain that is at least three-quarter full length. |
| WHOLE GRAIN INDEX | The percent of Whole Grain yield after milling. The index is in terms of the output of milled whole grains as a percent by weight of the input rough rice grains. |

*When used in an equation, * indicates multiplication.

4. BRIEF DESCRIPTION OF THE FIGURES

FIGS. 1A–1K Alkali Spreading Value Standards. FIGS. 1A–1B: Rating 2, No reaction. FIGS. 1C & 1D: Rating 3, Whole kernel with slight to moderate collar. FIGS. 1E & 1F: Rating 4, Split kernel with collar. FIG. 1G: Rating 5, Badly split kernel with collar. FIGS. 1H & 1I: Rating 6, Cotton center. FIGS. 1J & 1K: Rating 7, Clear center.

FIGS. 2A–2F Chalky Grain Standard. The figures show examples of typical white centered grains. (White belly grains are similar except the chalkiness tends to be on the belly side of the grains.) The grains shown are rated from 0 to 5. FIG. 2A: Rating 0, less than 5% chalk within a grain. FIG. 2D: Rating 1, about 10% chalk within a grain. FIG 2C: Rating 2, about 20% chalk within a grain. FIG. 2D: Rating 3, about 40% chalk within a grain. FIG. 2E: Rating 4, about 50% chalk within a grain. FIG. 2F: Rating 5, about 80% chalk within a grain. In Chalk Index determinations grains with 50% or more chalk content (i.e., grains rate $\geq 4$) are considered as chalky grains.

FIGS. 3A–3D The Correlation Between Starch Index (SI) With Peak, Hot Paste and Cool Paste Viscosities. The RVA and SI data points from fifty seven rice varieties are analyzed.

FIG. 3B The correlation between Peak viscosity (Y axis) and SI (X axis).

FIG. 3A The paradigm relationship between SI and amylograph viscosities.

FIG. 3D The correlation between Cool Paste viscosity (Y axis) and SI (X axis).

FIG. 3C The correlation between Hot Paste viscosity (Y axis) and SI (X axis).

FIG. 4 The Correlation Between Setback Amylograph Viscosity and the Starch Index. The RVA and SI data points from fifty seven rice varieties are analyzed. The setback viscosity is the Y axis and starch index is the X axis.

FIG. 5 The Correlation Between Gel Consistency and Starch Index. The "tube test" gel consistency and SI data points of twenty rice varieties are analyzed. The data are those presented at the 1979 International Rice Research Institute (IRRI) Rice Quality workshop. The data points for Basmati 370 are indicated by the arrows. Two regression equations and correlation coefficients for the relationship between gel consistency and amylose plus ASV are shown.

FIGS. 6A & 6B The Predicted Relationships Among Cooked Grain Firmness, Amylograph Setback Viscosity and Starch Index.

FIG. 6B A plot of the predicted cooked grain firmness (cooked with a water/rice ratio by volume of 1.75) and starch index from the data shown in Table 7.

FIG. 6A A plot of the predicted cooked grain firmness (cooked with a water/rice ratio by volume of 1.75) and amylograph setback viscosity from the data shown in Table 7.

FIG. 7 Yield Comparisons of Basmati 867 With Specialty and Commodity Rice Varieties. The data are the seed yields of Basmati 867 and the specialty or commodity variety that was cultivated in the same trial location.

FIG. 8 Head Milled Rice Yield Comparisons of Basmati 867 With Specialty and Commodity Rice Varieties. The data are the head milled rice yields of Basmati 867 and the specialty or commodity variety that was cultivated in the same trial location.

FIG. 9 The figure presents the Cooked Grain Dimension test results described in a study by the UK Flour Milling and Baking Research Association (The Authentication of Basmati Rice Using Near Infrared Transmittance Spectroscopy, FMBRA March 1993) and the result of a subsequent test by FMBRA of Basmati 867. The FMBRA test measures cooked grain dimensions and gives the results in terms of a shape factor measurement "Weighted Percent >42". FMBRA tested 95 varieties including 27 which FMBRA characterized as having the basmati cooked grain shape. The 95 varieties were ranked in order of shape factor and the rank is plotted on the Y axis. The X axis shows the corresponding shape factor. The horizontal dotted line shows the cut-off between basmati lines and non-basmati lines. The Basmati 867 rank (indicated by the arrow) is within the basmati region.

FIG. 10 The figure presents the results of a 1993 study by the UK Flour Milling and Baking Research Association (The Authentication of Basmati Rice Using Near Infrared Transmittance Spectroscopy, FMBRA March 1993) and the result of a subsequent test by FMBRA of Basmati 867. The 1993 FMBRA study measured amylograph curve shape of rice pastes prepared from 98 varieties including 12 which FMBRA characterized as being Indian and Pakistan basmati and six varieties which FMBRA characterized as being basmati substitute. The results are presented in terms of a factor D70 which relates to the peak area, and V120 which relates to the hot paste viscosity. The FMBRA test results were plotted on a diagram as shown in the figure and a basmati rice region was defined. Subsequently, FMBRA tested Basmati 867 and a number of other basmati rice products. The results are overlaid on to the previously defined diagram. The analysis show Basmati 867 falls within the FMBRA basmati rice amylograph region.

5. DETAILED DESCRIPTION OF THE INVENTION

The instant invention provides novel rice lines and the plants and grains of said lines. The rice lines of the invention combine desirable grain traits of basmati rice with desirable plant traits of semi-dwarf, long grain rice. In particular, the combined traits comprise the basmati grain traits of "popcorn" aroma, long slender grain shape, extreme grain elongation on cooking, and dry, fluffy (or firm) texture of the cooked grain and the semi-dwarf, long grain plant traits of short stature, photoperiod insensitivity, high grain yield, and disease tolerance. In addition to the desired basmati grain traits, the grains of the invention have superior characteristics of high whole grain index, low chalkiness and low burst index. The invention also provide a novel, convenient method for screening rice grains that can be cooked to the firmness of good quality basmati rice preparations and the use of said method in rice breeding program. In particular, the novel method is based on the discovery that the likely firmness and texture of cooked rice grain can be predicted by its "starch index" (SI), which consists of the sum of grain's percent amylose (PA) (excluding the effect of aging) and alkali spreading value (ASV).

The novel rice lines of the invention may be produced by classical plant breeding using basmati and semi-dwarf, long grain parents that have the desired grain and plant traits, respectively, and using selection schemes comprising the novel method for screening of the cooked grain texture trait. The invention is illustrated by examples that 1) compare plant and grain characteristics of basmati rice and long grain rice, 2) demonstrate the relationship between the starch index and cooked grain firmness, 3) account the breeding of several novel rice lines of the invention, and 4) examine the plant and grain characteristic of the a novel rice line of the instant invention.

The various embodiments of the claimed invention described herein are by the way of illustration and are not meant to limit the invention. Specifically, the preferred embodiments describe a number of features which an artisan may recognize as not being absolutely essential, but clearly advantageous. They include the parental lines and the selection scheme used in the disclosed breeding program. The utilities of the disclosed breeding and selection scheme are broadly applicable to crosses among a wide range of parental lines and to many permutations of the disclosed selection scheme. Given the instant teachings, one skilled in the art would know the appropriate equivalent parental lines, approaches and methods needed to practice the present invention. Further, many of the plant breeding methods and rice grain assays which could be used in part to practice the instant invention are variety- and grain-independent and are well known to those skilled in the art. See Briggs, F. N. and Knowles, P. F., *Introduction to Plant Breeding*, 1967, Reinhold Publishing Corporation; Allard, R. W., *Principles of Plant Breeding*, 1966, John Wiley and Sons, Inc.

5.1. Novel Rice Lines

A rice line of the invention is genetically substantially homozygous and thus can be reproduced by planting seeds of the line, growing the resulting plants under self-pollinating or sib-pollinating conditions, and harvesting the resultant seeds, using techniques know in plant breeding. The invented lines show phenotypic uniformity and stability within the limits for all traits described herein. The plant, seed, and grain characteristics described herein for the invented lines are the typical values for the invented lines cultivated in Puerto Rico or Alvin, Tex., or Newport, Ark., or Dewitt, Ark. or Belle Glade, Fla.

According to the invention, a rice line of the invention is semi-dwarf in stature. The mature plants of an invented line have an average height of less than about 150 cm, or preferably an average height of less than 115 cm, or more preferably an average height of less than 95 cm. In one embodiment, the mature rice plants have an average height of 115 cm. In another embodiment, the mature rice plants have an average height of 120 cm.

A rice line of the invention also is substantially photoperiod insensitive. The rice plants of an invented line flower at approximately the same age when planted any time within a relatively wide window of "planting season". More particularly, the plants of an invented line flower approximately 90 to 110 days and mature approximately 110 to 130 days after planting when planted in the northern hemisphere any time from the beginning of March to the end of June. In a particular embodiment, the rice plants flower approximately 95 days and mature approximately 124 days after planting. In another embodiment, the rice plants flower approximately 98 days and mature approximately 128 days after planting.

A rice line of the invention moreover is high yielding. When cultivated using standard North American production practices, the rice plants of an invented line produce an average dried rough rice grain yield of at least about 3,700 lbs/acre, or preferably at least about 5,000 lbs/acre, or more preferably at least about 6,000 lbs/acre. In one embodiment, the rice plants produce an average seed yield of about 5,300 lbs/acre. In another embodiment, the rice plants produce an average seed yield of about 5,400 lbs/acre.

A rice line of the invention further is disease tolerant. The rice plants of an invented line are moderately susceptible to blast and sheath blight, or preferably moderately tolerant to blast (*Pyricularia oryzae*), sheath blight (*Rhizoctonia oryzae*) and straighthead, or more preferably resistant to blast, sheath blight and straighthead. In particular embodiments, the rice plants of two invented lines are moderately tolerant to blast and sheath blight.

A rice line of the invention furthermore is high tillering. The rice plants of an invented line produce an average of at least 2 to 3 tillers per plant, or preferably an average of 4 tillers per plant, or more preferably an average of 5 or more tillers per plant. In particular embodiments, the rice plants of two invented lines produce an average of 4 tillers per plant when plant stands are about 20–30 plants per square foot.

A rice line of the invention further produce rough rice grains (seeds) that can be processed (i.e., dried, dehulled and milled) to yield a high percentage by weight of whole grain rice (WG). The rice plants of an invented line produce seeds that can be processed to yield grains containing an average of at least 40% WG, or preferably an average of at least 52% WG, or more preferably an average of at least 62% WG. In a particular embodiment, the rice plants produce seeds that can be processed to yield grains containing an average of about 50% WG. In another embodiment, the rice plants produce seeds that can be processed to yield grains containing an average of about 45% WG.

A rice line of the invention furthermore produces seeds that can be processed to grains with the characteristics described in section 5.2.

5.2. Rice Grains of the Invention

A rice line of the invention produce seeds which can be processed to grains comprising desirable characteristics traditionally identified with those of good quality basmati rice grains produced in the Indian subcontinent. Such grain characteristics include, but are not limited to, long thin grain shape, distinctively pleasing taste and aroma, extreme elongation of the cooked grain, and the dry and fluffy (or firm) texture of the cooked rice.

The various grain traits of the invented line described herein are those of dehulled and milled grain. The dehulling and milling of seeds to grains may be by any means known in the art. The grains of the invention are milled to between about 60 SMD and about 100 SMD, or their equivalents (see U.S. Pat. No. 5,208,063) when tested as white rice.

According to the instant invention, the rice grains of an invented line have an average milled grain length of at least about 6.65 mm, width of less than about 1.9 mm, and length/width (l/w) ratio of at least about 3.5. The rice grains of an invented line preferably have an average milled grain length of at least about 7.0 mm, width of less than about 1.75 mm, and l/w ratio of at least about 4.0. The rice grains of an invented line more preferably have an average milled grain length of at least about 7.3 mm, width of less than about 1.7 mm, and l/w ratio of at least about 4.3. In a particular embodiment, the rice grains have an average milled grain length of about 6.75 mm, width of about 1.85 mm, and l/w ratio of about 3.65. In another embodiment, the rice grains of invented line have an average milled grain length of about 7.26 mm, width of about 1.85 mm, and l/w ratio of about 3.92.

The rice grains of an invented line also have an average 2-acetyl-1-pyrroline content of at least about 150 parts per billion (ppb), or preferably at least about 400 ppb, or more preferably at least 800 ppb. In one embodiment, the rice grains have an average 2-acetyl-1-pyrroline content of about 400 ppb. In another embodiment, the rice grains have an average 2-acetyl-1-pyrroline content of about 150 ppb.

Moreover, rice grains of an invented line when cooked elongate lengthwise an average of at least 75%, or preferably 100%, or more preferably 120% over the uncooked grains. In a specific embodiment, the cooked rice grains of an invented line elongate an average of 90% over the uncooked grains. In another embodiment, the cooked rice grains of an invented line elongate an average of 75% over the uncooked grains.

The rice grains of the invented lines moreover have cooked grain texture and firmness comparable to that of good quality basmati rice preparations when cooked in the same manner. As described infra (see section 7.0.), the cooked grain firmness is related to Starch Index and can be so measured. Accordingly, the rice grains of an invented line have an average SI of at least about 27 with the SI consisting of an average percent amylose (PA) of at least 20 to 24 and an average alkali spreading value (ASV) of at least about 2.9 to about 7. The rice grains of an invented line preferably have an average SI of at least 30 with the SI consisting of an average PA of at least 23 to 27 and an average ASV of at least about 2.9 to about 7. The rice grains of an invented line more preferably have an average SI of at least 33 with the SI consisting of an average PA of at least 26 to 30 and an average ASV of at least about 2.9 to about 7. In an embodiment, the rice grains have an average SI of about 29 with the SI consisting of an average PA of about 24.5 and an average ASV of about 4.5. In another embodiment, the rice grains have an average SI of about 29 with the SI consisting of an average PA of about 26.2 and an average ASV of about 2.9.

The rice grains of an invented line when cooked also have an average burst index of less than about 4, or preferably less than about 3, or more preferably about 1. In a specific embodiment, the rice grains when cooked have an average burst index of about 2. In another embodiment, the rice grains when cooked have an average burst index of about 3.

The rice grains of the invented line further have low contents of chalked grains, a desired grain quality typically not found in premium basmati rice from India or Pakistan. Accordingly, rice grains of an invented line additionally have an average chalked grain content of less than 40%, or preferably less than 15%. In a specific embodiment, the rice grains have an average chalked grain content of about 8%. In another embodiment, the rice grains have an average chalked grain content of about 7%.

5.3. Breeding Novel Rice Lines

A novel rice line of the instant invention may be produced by plant breeding. Single, double, three-way and multi-line crosses involving many combinations of basmati and semi-dwarf, long-grain parent lines can be used to produce the rice lines of the invention. The novel rice lines of the invention may be bred from such crosses by repeated selection and propagation of seeds from segregants that show improvements over the preceding generation in one or more of the desired grain or plant traits (see sections 5.1. and 5.2.). Any selection and propagation method or scheme known in the art may be used. Useful methods range from single seed descent to bulk selection. Preferred methods such as modified bulk selection or pedigreed breeding should attain maximum differentiation of plant and grain types in early screening (i.e., generations), or large enough populations in bulk advance such that the extremely rare variants are likely to be retained in the breeding population.

5.3.1. Source Material

A rice line of the invention may be selected from a population pool produced by crossing a basmati line that has many or most of the desired basmati grain characteristics (e.g., strong 2-AP aroma, long slender grain shape, extreme elongation on cooking, and a firmed texture of the cooked grain (i.e., SI, PA and ASV)) with a semi-dwarf, long-grain line that has many or most of the desired plant characteristics (e.g., short stature, photoperiod insensitivity, high seed yield, disease tolerance, early maturity and moderate to high tillering). A preferred basmati parent is any that has all the desired grain traits described in section 5.2. A more preferred basmati parent is one that has all the desired grain traits in the preferred or more preferred ranges described in section 5.2. A most preferred basmati parent is one that additionally has one or more of the desired plant traits described in section 5.1. Similarly, a preferred semi-dwarf, long grain parent is any that has all the desired plant traits described in section 5.1. A more preferred semi-dwarf, long grain parent is one that has all the desired plant traits in the preferred or more preferred ranges described in section 5.1. A most preferred semi-dwarf, long grain parent is one that additionally has one of more of the desired grain traits described in section 5.2 or that does not sun check at maturity, thus increasing whole grain milling yields.

Accordingly, a basmati line including but not limited to any of those shown in Table 1 may be used as the basmati parent, and a semi-dwarf, long grain variety including but not limited to any of those shown in Table 2 may be used as the semi-dwarf, long grain parent. A preferred basmati parent may be Bas122 (PI385418), Bas433 (PI385455) or (PI392153). In a specific embodiment, Bas433 (PI385455) is used as the basmati parent. In another embodiment, Bas397 (PI385452) is used as the basmati parent. In a specific embodiment, CB801 is used as the semi-dwarf long grain parent in the first cross and CB801E is used as the semi-dwarf, long grain parent in the subsequent topcross. In another embodiment, GP1130 is used as the semi-dwarf, long grain parent in the first cross and LEAH is used as the semi-dwarf, long grain parent in the subsequent topcross.

crosses) using one or more basmati lines and one or more semi-dwarf, long grain lines. A single cross between a basmati parent and a semi-dwarf, long grain parent may be used. Preferably, the pool is produced by a topcross of second semi-dwarf, long grain variety to the progenies of a cross between a basmati parent and a long grain parent.

TABLE 1

Basmati Lines Suitable for Breeding Novel Rice Lines

| Variety | PI Number | PA | ASV | Starch Index | Length[1] Dry | Cooked | % Elong.[2] |
|---|---|---|---|---|---|---|---|
|  | PI392151 | 28.6 | 6.5 | 35.1 | 4.7 | 8.5 | 81 |
| BAS 138 | PI385817 | 29.1 | 5.5 | 34.6 | 6.6 | 10.1 | 53 |
| BAS 208 | PI385427 | 27.4 | 5.0 | 32.4 | 6.2 | 13.5 | 118 |
| BAS 376 | PI385447 | 25.2 | 7.0 | 32.2 | 5.9 | 12.7 | 115 |
| BAS 427 | PI385454 | 25.0 | 7.0 | 32.0 | 5.8 | 14.3 | 147 |
| BAS 375A | PI385446 | 25.9 | 5.5 | 31.4 | 5.8 | 13.7 | 136 |
| — | PI385778 | 26.4 | 5.0 | 31.4 | 6.4 | 14.8 | 131 |
| BAS-10-123 | PI385419 | 25.8 | 5.0 | 30.8 | 6.4 | 14.8 | 131 |
| BAS-10-24 | PI385786 | 25.7 | 5.0 | 30.7 | 7.0 | 15.3 | 119 |
| BAS 375 | PI385445 | 25.7 | 5.0 | 30.7 | 6.1 | 13.1 | 115 |
| BAS 122 | PI385418 | 23.7 | 7.0 | 30.7 | 5.9 | 13.6 | 131 |
| BAS 334 | PI385436 | 25.6 | 5.0 | 30.6 | 6.3 | 13.3 | 111 |
| BAS 213 | PI385429 | 25.7 | 4.5 | 30.2 | 6.6 | 14.6 | 121 |
| BAS 372 | PI385443 | 25.7 | 4.5 | 30.2 | 6.5 | 13.8 | 112 |
| BAS 397 | PI385452 | 23.1 | 7.0 | 30.1 | 5.9 | 13.7 | 132 |
| BAS 433 | PI385455 | 26.1 | 3.8 | 29.9 | 6.9 | 16.2 | 135 |
| BAS 242 | PI385430 | 24.9 | 5.0 | 29.9 | 6.4 | 13.6 | 113 |
| BAS 406 | PI385806 | 24.6 | 4.5 | 29.1 | 6.4 | 13.4 | 109 |
| BAS 443 | PI385456 | 23.9 | 4.7 | 28.6 | 6.8 | 13.9 | 104 |
| BAS 388 | PI385450 | 23.3 | 4.0 | 27.3 | 6.6 | 14.2 | 115 |
| — | PI392153 | 21.2 | 5.3 | 26.5 | 6.1 | 12.0 | 97 |
| — | PI392144 | 20.8 | 5.0 | 25.8 | 6.1 | 12.6 | 106 |

[1]Length is the average grain length in mm.
[2]% Elong. is the average grain elongation with cooking.

TABLE 2

Long Grain Varieties Suitable for Breeding Novel Rice Lines

| Variety | PA | ASV | Starch Index | Total[1] Milling | Whole[2] Milling |
|---|---|---|---|---|---|
| CICA-6 | 29.5 | 7.0 | 36.5 | 71 | 62 |
| L202 | 29.5 | 3.3 | 32.8 | 69 | 58 |
| CB801E | 26.6 | 3.8 | 30.4 |  |  |
| CB801G | 27.3 | 3.1 | 30.4 |  |  |
| LEBONNET | 25.2 | 4.4 | 29.6 |  |  |
| LEMONT | 25.6 | 3.0 | 28.6 | 70 | 61 |
| CB801 | 24.9 | 3.0 | 27.9 | 68 | 57 |
| L201 | 23.5 | 3.7 | 27.2 | 69 | 55 |
| LABELLE | 24.5 | 2.7 | 27.2 | 67 | 60 |
| CB860 | 23.6 | 3.0 | 26.6 |  |  |
| LC770AC38-30 | 23.3 | 2.8 | 26.1 |  |  |
| IR841-85-1-1 | 19.8 | 6.1 | 25.9 |  |  |
| P33-C-19 | 19.8 | 6.0 | 25.8 | 66 | 53 |
| LEAH | 21.3 | 4.0 | 25.3 |  |  |
| P33-C-30 | 18.7 | 6.0 | 24.7 | 65 | 56 |

[1]Percent milled grain yield.
[2]Percent whole grain yield.

Additional lines that can be used as the semi-dwarf, long-grain parent in either the initial cross or topcross include recently released U.S. varieties such as RT7015, Kaybonnet, Cypress and Katy, as well as indica types from Asia which meet some or all of the plant criteria indicated above. Semi-dwarf varieties with aroma (2-AP) can also be used. Again, preferred types would be those with acceptable plant characteristics and with grain dimensions and starch properties (PA, ASV and Starch Index) similar to the basmati.

5.3.2. Selection of Novel Rice Lines

A useful population pool may be generated by any crossing protocol (e.g., single, topcross, backcross, and multi-line Following the initial cross or crosses, selected plants in each of the ensuing generations are allowed to self-pollinate. This enables trait segregation and, eventually, genotypic and phenotypic stabilization. The invented lines may be produced by repeated cycles of selection and propagation of segregants exhibiting the desired plant and grain traits described in sections 5.1 and 5.2. The cultivation of all generations of a breeding pool may be done in the field. The F1 and topcross-F1 plants preferably are cultivated in the greenhouse.

The selection for the desired grain and plant traits (as specified in sections 5.1 and 5.2) in the ensuing generations may be by any known methods and the trait selections done in any combination and order. For details of the selection and screening methods that may be used see section 5.4. A preferred selection sequence is to screen for desired plant type including short stature, early maturing, etc. in the F1; for desirable plant traits such as photoperiod insensitivity, plant height, tiller number and/or seed set in the earlier generations (i.e., topcross-F1 & F2); for plant traits such as adaptation, seed yield, maturity and erect plant type and grain traits such as aroma, grain length and shape, whole grain milling, starch index, and cooked grain elongation in the middle generations (i.e., F3 to F7); and for all desirable plant and grains traits in the later generations (i.e., F7 to F11).

Further, an important part of the selection process is to control for environmental effects when a particular generation of plant is being grown and subsequently evaluated. This is accomplished by planting, alongside the trial plants, known control varieties covering a similar range of maturities and harvesting their seeds as they mature in tandem with those of the test plants. As environmental variations will tend to affect the expression of some of selected for characteristics (e.g., grain starch properties, milling yields, grain yields, tillering, plant height) in control and test plants in similar ways. This use of parallel control lines assists in the evaluation process. The control lines are used in performance evaluations for field yields, other agronomic traits, etc. as well as for the samples used in laboratory analysis for quality traits. Replication of tests and proper statistical analysis will generally provide the means of discerning the confidence level in a particular test, and the control varieties are important in this analysis also. Control varieties are typically those varieties commonly commercially grown in the region of the tests.

The advancing of traits throughout the stages of advancement for segregates vary for each set of genetic materials. Table 10 lists the primary selection criteria at each generation of advancement. In general the criteria as established herein in the definition of a desired basmati line are the same criteria used in the selection process from generation to generation with the elimination levels becoming more severe as the list of candidates is progressively narrowed in the advanced generations.

The number of plants screened and advanced are increased at various stages in the breeding program. The initial F1 cross or topcross-F1 cross should involve at least 40 crosses of 10 lines, preferably 80 crosses of 20 lines. The number of F1 plants screened should be at least 500 or preferably over 1,000. The number of F2 plants screened should be at least 500 plant rows or preferably 1,000 plant rows which should provide a total F2 population of over 250,000 individual plants. The number of F3 plants screened should be at least that produced from 1,500 selected F2 panicles or preferably from 3,000 selected F2 panicles. The number of F4 plants screened should be at least that produced from 5,000 selected F3 panicles or preferably from 10,000 selected F3 panticles. The number of F5, F6 and F7 plants screened should be at least that produced by 10,000 rows selected from the preceding generation plants, or preferably by 15,000 rows selected from the preceding generation. The number of F8 and F9 plants selected and screened can be decreased with each succeeding generation as field testing and quality laboratory analyses will eliminate the now homozygous lines that do not meet the criteria established for all traits defined herein. The number of F8 lines evaluated should be at least that produced from 500 selected F7 lines and preferably from 750 F7 lines. The number of F9 lines evaluated should be at least that produced from 50 selected F8 lines and preferably from 100 F8 lines. The number of F10 lines should be at least that produced from 20 selected F9 lines and preferably from 50 F9 lines. The number of F11, F12, F13 and F14 lines should be produced from the best five F10 lines which can be increased for commercial production and maintenance of pure seedstocks.

Starting with the F9 generation, selected plants exhibiting all the desired plant and grain traits (see sections 5.1. and 5.2.) may be sufficiently homozygous for use in seedstock production. Preferably, selection for all desired plant and grain traits as well as field production traits is continued to the F11 generation before a plant with all the desired traits is selected and increased as a designed homozygous line for commercial production.

5.4. Assays of Plant and Grain Traits

The screening of the plant and grain traits may be by any means and methods known. The ability to precisely quantify desired grain traits in very early and in later generations may be vital to the success of the breeding program. Similarly, the ability to do a complete quality analysis on single plants may also be critical in as much as it significantly improves the chances of finding the extremely rare segregates which exhibit all or an optimum combination of the desired plant and grain traits. Thus, preferred screening methods are those that are highly precise and sensitive and that require minute amounts of sample material. Examples of such preferred methods include the use of gas chromatography to quantify to the part per billion (ppb) level the amount of 2-AP in the grains of a single plant and the use of video image analysis to rapidly and accurately measure uncooked and cooked grain dimensions. Additional preferred methods include the use of near infrared spectroscopy (NIR) to determine percent amylose and also the use of the Starch Index (SI) in early and later generations to precisely predict the cooked grain texture (i.e., firmness).

The procedures described below are by the way of illustration and not limitation. They may be substituted by known equivalent procedures.

5.4.1. Grain Dimension Determinations

Grain shape and dimensions may be measured or screened in the early generations of a breeding program by manually threshing the seed and measuring the dehulled grain.

Grain dimensions preferably are determined using an image analyzer system comprising a video capture unit (Imaging Technology, Inc., Bedford, Mass.), with black and white video camera, a video monitor, a light box, and a computer running the Optimas program (Bioscan, Inc., Edmonds, Wash.). The measurements are carried out on whole milled grains, milled to the well milled level used during the determination of whole grain yield assay (see section 5.4.2.). Measurements are made of grain width and major axis length (grain length). Preferably at least 25 grains per sample are measured and used to determine the mean value for a sample.

5.4.2. Whole Grain Yield Assay

The procedure assays the yield of whole grains after milling. The milling is carried out on a McGill #2 milling machine as follows:

1. A rough rice sample with moisture content of 12.5% or less is cleaned of debris or light grains by aspiration.
2. The sample is allowed to equilibrate to the temperature and humidity of the air conditioned milling room.
3. The milling machine is set for long grain rice (following established USDA standards), i.e., by placing the 1,500 gm weight on the mark for long grain type on the weight bar.
4. The machine is pre-warmed by milling two to three samples of discarded rice.
5. 162 grams of sample rice is milled for 58 seconds.
6. The milled sample is allowed to cool for about 10 minutes then weighted to determine the total milled weight.
7. The milled sample is sifted to separate broken and whole grain on sizing device or screens. The sample is first passed over a #10 screen and then a #12 screen. The sifting may be repeated a second time. The retained material, which contain three-quarter sized or larger grains, is classified as whole grains or head milled rice.
8. The whole grain fraction is weighed and the whole grain yield is calculated as the percent of the total milled weight. Preferably two samples per line or plant are assayed and the average of the two samples is used in the evaluation process.

5.4.3. Percent Amylose (PA) Determination

The grain amylose content may be determined using an adaptation of the procedure described by Juliano (1971, A simplified assay for milled rice Amylose, Cereal Sci. 16:334). The procedure may be carried out as follows:

1. 60 mg ground rice (sifted through a 100+ mesh screen) is suspended in 1 ml of ethanol and mixed with 5.4 ml of 1N NaOH and allowed to incubate at room temperature for 10 min.
2. The sample is heated for 10 minutes in a boiling water bath, allowed to cool and then brought up to exactly 60 ml with deionized distilled water and mixed thoroughly. The sample is allowed to stand at room temperature for at least 2 hours.
3. 5 ml of the vigorously resuspended sample is mixed with 1 ml of 1N acetic acid, 2 ml of "iodine" solution (0.2% I, 2% KI) and 92 ml of distilled water. The sample is incubated at room temperature for 20 minutes.
4. Sample absorption at 620 nm is measured in a spectrophotometer against a blank consisting of 2 ml of the iodine solution and 1 ml 1N acetic acid diluted to 100 ml with distilled water.
5. The 620 nm absorption is converted to amylose concentration using a standard absorption curve based on purified potato amylose (NBC) (Sigma Chemical Co. or Stein Hall and Co., Inc.).
6. Percent amylose equals 100×weight of amylose/weight of sample. Preferably two samples per line or plant are assayed and the average of the two samples is used in the evaluation process.

5.4.4. Alkali Spreading Value (ASV) Determination

The grain ASV may be determined using an adaptation of the procedure described by Littie et al. (1958, Differential effect of dilute alkali on 25 varieties of milled rice, Cereal Chem. 35: 111–126). The procedure may be carried out as follows:

1. 6 rice grains (whole or otherwise) are placed in small tray and suspended in approximately 10 ml of 1.7% potassium hydroxide.
2. The grains are arranged so that no contact occurs among the grains and allowed to incubate at room temperature overnight.
3. The degree of spreading of each of the grains is visually scored numerically from 2 to 7, minimum to maximum according to the to the standards shown in FIGS. 1A–1K.
4. The ASV of a sample is the average of the scores of the 6 grains.

Preferably multiple samples per line or plant are assayed and the average of the samples is used in the evaluation process.

5.4.5. 2-Acetyl-1-Pyrroline (2-AP) Determination

The 2-AP content of rice grains may be evaluated in the field by tasting the raw seed. Preferably, 2-AP content of rice grains is determined by gas chromatography (GC) as follows:

1. 0.3 grams (gm) of a coarsely ground milled grain sample is mixed with 0.5 ml of methylene chloride containing 1 part per million 2,4,6-trimethyl pyridine (TMP) in a gas chromatograph vial and the vial sealed.
2. The sealed vial is heated at 85° C. for 2 hr.
3. A four microliter sample of the cooled liquid extract is analyzed in a Hewlett Packard HP 5890 II Gas Chromatograph using a fused silica capillary column (SGE, 30 m length×0.53 mm i.d.×2.65 um film thickness), a oven temperature ramp from 45° C. to 210° C., injector temperature of 210° C. and a flame ionization detector at 250° C.
4. The 2-AP is identified and measured relative to the TMP peak using the following equation:

$$\text{2-AP (ppm)} = (\text{2-AP area/TMP area}) \times (0.916 \text{ (TMP density)}) \times (0.5(\text{sample vol.}))/(\text{dry weight of grain sample})$$

Preferably multiple samples per line or plant are assayed and the average of the samples is used in the evaluation process.

5.4.6. Cooked Grain Elongation Assay

The percent elongation of cooked grains may be determined as follows:

1. Place rice grains in a cuvette, soak grains in room temperature deionized water for 30 minutes.
2. Place cuvette with grains in boiling water bath and cook for 12 minutes.
3. Soak cooked samples in tray of room temperature deionized water for 2 minutes. Measure the length of cooked grains.
4. Subtract the combined length of 10 uncooked grains from the combined length of 10 cooked grains. Divide the difference by the combined uncooked grain length for percent (%) elongation.

Preferably multiple samples per line or plant are assayed and the average of the samples is used in the evaluation process.

5.4.7. Cooked Grain Texture or Firmness Assay

The texture of firmness of cooked grains may be determined using a Pabst Texture Tester (Model TT2P; R. E. Pabst, Houston, Tex.) as follows:

1. Place ten grams of cooked rice into the Texture Tester cartridge and transferred into the cell chamber.
2. Once the sample temperature has stabilized, the compression cycle is started. The sample is compressed three times to three different levels (i.e., 50%, 75%, and 100%).
3. Data is recorded as the force required to compress the sample at each of the three compression levels.
4. The force measurements at 75% and 100% compressions are averaged and reported as Pabst Texture measurement for firmness.

5.4.8. Amylography of Rice

Amylography of rice grains may be carried out using a Rapid Visco Analyser (RVA) (manufactured by Newport Scientific, Australia and distributed in the USA by Foss Food Technology (Eden Prairie, Minn.)). The software used to run the viscosity program is Thermocline and the data handling software is Thermoview. The procedure is as follows:

1. 3.5 gms of ground grains (ground through 0.5 mm screen on a Udy mill) is mixed with 25 ml of distilled water and stirred to form a uniform paste.
2. The rice paste is place in the sample chamber of RVA and heated to 60.0° C., at which point the viscosity of the paste over a twenty minute heating/cooling cycle is analyzed. The temperature program is as follows: heat to 60.0° C. by the 1.0 min. point; heat to 80.0° C. by the 7.0 min. point; heat to 95.0° C. by the 8.0 min. point; maintain at 95.0° C. to the 12.5 min. point; cool to 50.0° C. by the 15.0 min. point; and hold at 50.0° C. to the end of the cycle at the 20.0 min. point.
3. The following parameters may be determined from the recorded amylograph:

Hot Paste Viscosity is the value at the lowest point of the curve.

Cool Paste Viscosity is the value at the 18.5 minute mark.

Peak Viscosity is the highest viscosity reached during the entire run.

Setback is the Peak Viscosity subtracted from the Cool Paste viscosity.

5.4.9. Bursting Index Determination

The tendency of grains to burst upon cooking is dependent upon the cooking conditions, which includes the amount of water used to cook the grain. This assay standardizes the amount of water used that, according to an empirical determination based on the Starch Index of the sample, would produce cooked rice with a Pabst firmness of 7.6. The tendency of grains to burst upon cooking is evaluated as follows:

1. Determine amount of the water needed to cook one cup of grain according to the Starch Index of the sample using the formula Water/Rice ratio by volume=1.75+ 0.053×(SI−29).
2. Soak grain in the determined amount of water for 20 minutes.
3. Cook grains to an end point temperature of 104.2° C. in a Precision Cooking Systems rice cooker model PCS-T, following manufacturer's instructions.
4. Five minutes after completion of cooking, randomly select approximately 10 to 12 grams of cooked grains with tweezers or a spatula and place sample grains in a dish and cover sample grains with water to prevent desiccation.
5. Visually evaluate grains by comparing to the following Bursting Index (1–9).

1=100% of grains intact, smooth and straight.

2=80–90% of grains intact, 10–20% of grains with frayed and split ends.

3=60–70% of grains intact, 30–40% of grains with frayed and split ends.

4=50–60% of grains intact, 40–50% of grains with frayed and split ends.

5=50% of grains intact, 50% of grains with frayed and split ends.

6=40–50% of grains intact, 50–60% of grains with frayed and split ends.

7=30–40% of grains intact, 60–70% of grains with frayed and split ends.

8=10–30% of grains intact, 70–90% of grains with frayed and split ends.

9=No grains intact.

5.4.10. Chalk Index Determination

The chalkiness of a grain sample may be determined as follows:

1. Select whole grains from a sample and place approximately ten grams of whole grains on a light box.
2. Visually identify grains with 50% or more chalk content (can be white belly or white centers) according to standard (see FIGS. 2A–2F) These are scored chalky as grains and separated from the other grains.
3. Weigh chalky grains and calculate the percent chalkiness of sample by weight.

5.4.11. Starch Index and its Use in Predicting Cooked Grain Firmness

The Starch Index (SI) of a grain sample consists of the sum of the percent amylose (PA) and the alkali spreading value (ASV) of the sample. Its utility in rice breeding is based on the surprising discovery that it predicts the likely firmness and texture to which the grain sample can be cooked. The studies that lead to this discovery are detailed in Example 2 (see section 7.0., particularly section 7.4.).

6. EXAMPLE 1: COMPARISON OF BASMATI AND AMERICAN LONG GRAIN RICE CHARACTERISTICS

Table 3 compares typical measurements of the PA, ASV, SI, cooking properties and grain dimension of traditional high quality basmati rice grains produced in Indian or Pakistan and marketed as high quality basmati in the United Kingdom and the United States, as compared to Lemont which is a typical non-aromatic U.S. long grain variety. In the comparison, the basmati grains have a higher length to width ratio in the uncooked state and higher elongation during cooking than the typical U.S. long grain. Moreover, the basmati grains' ASV values are significantly higher and the Setback values greater (i.e., cool paste amylograph viscosity is higher than the peak viscosity) than that of Lemont. The Tilda® rice grains assayed are more highly milled but also contain partially chalky grains (white center). In general the commercial basmati grains from India and Pakistan are variable in color and degree of milling with a lower transparency level and higher levels of chalky grains (and in some cases surface bran) than U.S. long grain rice. The significance of these measurements relative to the invented rice line is assessed in section 9.

TABLE 3

TYPICAL BASMATI AND U.S. LONG GRAIN PROPERTIES

| BRAND OR VARIETY | MILLED LENGTH (mm) | MILLED WIDTH (mm) | MILLED L/W | COOKED GRAIN ELONG. (%) | SATAKE MILLING DEGREE | SATAKE WHITE-NESS | SATAKE TRANS-PARENCY |
|---|---|---|---|---|---|---|---|
| TYPICAL AGED BASMATI RICE | | | | | | | |
| ELEPHANT | 7.05 | 1.79 | 3.94 | 85 | 80 | 38 | 2.0 |
| TILDA | 7.72 | 1.84 | 4.20 | 112 | 102 | 41 | 3.3 |
| UNCLE BEN | 7.42 | 1.73 | 4.29 | 101 | 88 | 39 | 2.4 |
| STORE BRND | 7.13 | 1.75 | 4.07 | 110 | 68 | 35 | 1.2 |
| TYPICAL U.S. LONG GRAIN RICE | | | | | | | |
| LEMONT | 6.60 | 2.15 | 3.07 | 50 | 113 | 43 | 3.6 |

| BRAND OF VARIETY | AMYLOGRAPH - RVA | | | | STARCH PROPERTIES | | |
|---|---|---|---|---|---|---|---|
| | PEAK | HOT | COOL | SETBACK | PA | ASV | SI |
| TYPICAL AGED BASMATI RICE | | | | | | | |
| ELEPHANT | 208 | 181 | 404 | 124 | 22.6 | 7.0 | 29.6 |
| TILDA | 314 | 145 | 325 | 11 | 23.3 | 6.5 | 29.8 |
| UNCLE BEN | 337 | 183 | 399 | 62 | 23.4 | 6.6 | 30.0 |
| STORE BRND | 343 | 165 | 371 | 28 | 22.6 | 6.3 | 29.9 |
| TYPICAL U.S. LONG GRAIN RICE | | | | | | | |
| LEMONT | 433 | 127 | 266 | −167 | 23.6 | 3.8 | 27.4 |

EXAMPLE 2: THE RELATIONSHIP BETWEEN GRAIN STARCH PROPERTIES AND COOKED GRAIN TEXTURE OR FIRMNESS

7.1. Effects of Growing Location and Date of Harvest on Grain Starch Properties A study of the properties of Lemont and RT7015, both are semi-dwarf, long grain varieties, in test locations from Florida to Texas to North Arkansas, with the crop harvested at dates varying from August to November, demonstrates the impact of growing environment on starch properties. (Grain starch properties were assayed according to procedures described in section 5.4.) Alkali spread values of these crops varied from 2.4 to 6.5 and percent amylose from 23.4 to 26.7. The varieties were tested together and the properties essentially changed together. Late harvesting and more northerly locations generally gave the highest levels of PA and ASV, the lowest values of amylograph peak and hot paste viscosity and the highest values of cool paste viscosity. Peak viscosity was the most affected measurement and ranged from about 325 to 425 across environments.

Table 4 shows an example of the impact of April and July date of planting (harvested in August and November, respectively) in Texas on the average starch properties of five semi-dwarf, long grain varieties with maturities ranging from about 110 to 125 days.

TABLE 4

EFFECT OF DATE OF SEEDING/HARVEST ON RICE STARCH PROPERTIES[1]

| | AUGUST[2] HARVEST | NOVEMBER[3] HARVEST |
|---|---|---|
| PERCENT AMYLOSE (PA) | 24.0 | 24.5 |
| ASV | 4.1 | 6.4 |
| SI = PA + ASV | 28.1 | 30.9 |

TABLE 4-continued

EFFECT OF DATE OF SEEDING/HARVEST ON RICE STARCH PROPERTIES[1]

| | AUGUST[2] HARVEST | NOVEMBER[3] HARVEST |
|---|---|---|
| AMYLOGRAPH | | |
| GEL TEMP | 74.7 | 71.2 |
| PEAK | 427 | 342 |
| HOT | 131 | 133 |
| COOL | 297 | 297 |
| SETBACK | −130 | −45 |

[1]The data shown is the average of 5 lines planted in Texas.
[2]Planted in April.
[3]Planted in July.

7.2. Effect of Aging on Amylograph Starch Properties

The impact of aging on starch properties is shown in Table 5. Seven long grain products were milled shortly after harvest and artificially aged by storing in sealed jars in a 35° C. oven for up to 37 or 70 days. A small increase in ASV (about 1 Unit) was noted with aging. Rice with a higher peak viscosity and a more negative setback due to aging cooks firmer and fluffier than less well aged rice. This is converse of the relationship found in fresh grains where grains with a higher positive setback cook firmer and fluffier than those with a lower setback (see section 7.3). The literature suggests that increases in amylograph viscosities with aging is associated with changes in lipid composition. This may account for the peculiar viscosity-firmness relationship of aged rice.

TABLE 5

EFFECT OF AGING ON RICE AMYLOGRAPH PROPERTIES[1]

|  | AGING PERIOD | | |
|---|---|---|---|
|  | 0 | ~37 DAYS | ~70 DAYS |
| AMYLOGRAPH | | | |
| PEAK | 347 | 401 | 421 |
| HOT | 140 | 146 | 155 |
| COOL | 297 | 316 | 337 |
| SETBACK | −50 | −85 | −84 |

[1]The data are the average of 7 lines whose average PA = 23.9, average ASV = 3.0 and average SI = 26.9.

7.3. Effect of Milling on Amylograph Starch Properties and Cooking Behavior of Rice The impact of degree of milling on grain starch properties is shown in Table 6. A Satake Milling Degree Meter was used to measure various degrees of milling (zero for brown rice). Samples were milled from a single lot. Lots (or varieties) which differ in core rice color and chalkiness can give misleading milling degree results using the Satake Milling Degree Meter.

TABLE 6

EFFECT OF DEGREE OF MILLING ON STARCH PROPERTIES[1]

|  | 0 | 48 | 79 | 96 | 118 |
|---|---|---|---|---|---|
| SATAKE MILLING DEGREE | | | | | |
| PA | 23.0 | 22.6 | 23.4 | 23.2 | 23.4 |
| ASV | 2.6 | 3.9 | 3.9 | 3.6 | 3.6 |
| SI = PA + ASV | 25.6 | 26.5 | 27.3 | 26.8 | 27.0 |
| AMYLOGRAPH | | | | | |
| PEAK | 313 | 388 | 402 | 418 | 422 |
| HOT | 110 | 133 | 136 | 142 | 145 |
| COOL | 244 | 304 | 264 | 265 | 267 |
| SETBACK | −69 | −84 | −138 | −153 | −155 |

[1]The study was done on long grain variety RTA 1002.

Table 6 shows that milling increases peak and hot paste viscosities and decreases the setback value. The effect is particularly evident with the initial milling of the grain as the bran and lipid rich layers are removed. Given that it is known that less milled rice cooks firmer and fluffier, this observation suggests that cooked grain texture may be associated with setback value, with firmer and fluffier textures positively correlated with higher setback values. That is rice with a lower peak viscosity and greater setback (less milled) will cook firmer than one with a higher peak viscosity and lower setback (well milled). The milling effect on viscosity-firmness relation in fresh rice is the reverse of the aging effect.

7.4. Starch Index and Cooking Behavior

The relationship between amylose level and rice cooking behavior is well known (see section 2.1.). The effect of gelatinization temperature (which correlates inversely with ASV) has also been observed, with a lower gelatinization temperature being associated with faster cooking. Basmati rice cooks relatively quickly and this has been associated with the fine grain dimensions and the low gelatinization temperature (high ASV). It would at first appear that the PA and ASV of traditional basmati rice grown in India and Pakistan should be matched if an acceptable product is to be grown outside of that area.

However, we have discovered that the amylograph of a rice variety with a percent amylose (PA) of 22 and an ASV of 7, tends to have a similar paste amylograph and cooked rice firmness at a given water/rice ratio as a rice variety with a percent amylose of 26 and an ASV of 3. This surprise finding indicates that the cooking behavior obtained from a traditional basmati rice grown in India or Pakistan with an ASV of 7 could be essentially obtained from a variety grown in an environment where the ASV is lower, by breeding a variety with a higher amylose content plus the other key basmati grain attributes.

The mutually compensating effect of PA and ASV indicates that the sum of PA and ASV, which we design as the Starch Index (SI), correlates with grain amylograph and cooking behavior characteristics. That relationship is confirmed by the following results.

Table 7 summarizes the outcome of regression analysis amylograph data conducted on (i) a range of twenty two widely differing rice varieties at the USDA Rice Research Laboratory, Beaumont, Tex. using a Brabender Amylograph (Six Decades of Rice Research in Texas—Research Monograph #4—June 1975) and (ii) similar tests using a Rapid Visco Analyzer on fifty seven varieties at RiceTec, Inc. The percent amylose of all these varieties ranged from 15 to 27, the ASV from 2.2 to 7.0, and the Starch Index from 17 to 34. The Brabender and RVA tests give different viscosity values but similar conclusions can be drawn from the results. Namely, that the Starch Index can be used to predict amylograph paste cooking behavior of different rice varieties. FIGS. 3A–3D show the individual RVA data points summarized in Table 7. Note that the relationships show more variability when the Starch Index is above 31. Grains with high SI are firmer cooking with a hard gel consistency and require a higher water/rice ratio for cooking to a given firmness than those with low SI.

TABLE 7

REGRESSION ANALYSIS OF AMYLOGRAPH DATA AND THE PREDICTED VISCOSITIES OF TWO RICE PASTES

| | | VISCOSITIES[4] | |
|---|---|---|---|
| REGRESSION EQUATIONS | | 22 PA, 7 ASV | 24 PA, 5 ASV |
| [1]B PEAK = 1422 − 22.4 PA − 18.5 ASV | [3]$R^2$ = 71% | 800 | 792 |
| B PEAK = 1446 − 22.6 SI | $R^2$ = 70% | 791 | 791 |
| [2]RVA PEAK = 705 − 13.1 PA − 11.8 ASV | $R^2$ = 69% | 334 | 332 |

TABLE 7-continued

REGRESSION ANALYSIS OF AMYLOGRAPH DATA AND THE PREDICTED VISCOSITIES OF TWO RICE PASTES

| REGRESSION EQUATIONS | | VISCOSITIES[4] | |
|---|---|---|---|
| | | 22 PA, 7 ASV | 24 PA, 5 ASV |
| RVA PEAK = 703 − 12.8 SI | R2 = 68% | 332 | 332 |
| B HOT = 366 + 3.0 PA − 3.7 ASV | R2 = 30% | 406 | 419 |
| B HOT = 325 + 3.3 SI | R2 = 16% | 421 | 421 |
| RVA HOT = 114 − 0.3 PA + 5.0 ASV | R2 = 6% | 142 | 132 |
| RVA HOT = 107 + 0.9 SI | R2 = 2% | 133 | 133 |
| B COOL = 617 + 9.5 PA − 11.6 ASV | R2 = 67% | 745 | 787 |
| B COOL = 489 + 10.3 SI | R2 = 35% | 788 | 788 |
| RVA COOL = 20 + 8.3 PA + 15.3 ASV | R2 = 35% | 310 | 298 |
| RVA COOL = 11 + 9.9 SI | R2 = 34% | 298 | 298 |
| B SETBACK = −805 + 31.9 PA + 6.9 ASV | R2 = 77% | 55 | 6 |
| B SETBACK = −6 + 1.0 SI | R2 = 83% | 23 | 23 |
| RVA SETBACK = −685 + 21.4 PA + 27.1 ASV | R2 = 86% | 25 | 36 |
| RVA SETBACK = −692 + 22.7 SI | R2 = 85% | −34 | −34 |

[1]B is USDA Brabender data.
[2]RVA is RiceTec data.
[3]R2, correlation coefficient.
[4]Predicted amylograph viscosities as per the regression equations based on the indicated PA and ASV.

FIG. 4 shows that the Setback amylograph measurement (Cool—Peak) has the highest correlation coefficient with Starch Index. Analyses show that inclusion of the ASV value improves predictability from 77% to 84% as compared to utilizing percent amylose alone.

Additional perspective on the relationship between PA, ASV, SI and other starch property measurements has been derived by analyzing data presented at the 1979 IRRI Rice Quality Workshop. The data comprised the ASV, PA and gel consistency of twenty rice varieties including Basmati 370 grown in both Philippine and Pakistan. FIG. 5 shows the data. The effect of ASV on gel consistency is greater than that of PA but the Starch Index also show significant correlation with gel consistency, with higher SI indicating lower gel consistency and a harder gel.

The effect of PA and ASV on cooked grain properties was determined by cooking a set of six long grain rice varieties. The varieties varied in properties, ranging from 18.6 PA to 30.4 PA, 3.6 ASV to 7.0 ASV and 25 SI to 36 SI. Each was milled to four different SMD of milling, and cooked at three different water/rice ratio. The firmness of the cooked rice was measured with Pabst Texture Tester. The regression equation for the Pabst firmness results at a cooked rice temperature of 50° C. was:

Pabst Firmness=14.2 +(0.57*PA)+(0.40*ASV)−(0.04*Satake Milling Degree)−(10.6*Water/Rice Ratio by Volume)

The coefficients for PA and ASV are similar and in the same direction indicating that rice grains with a similar Starch Index will cook to a similar firmness at a given water/rice ratio.

According to the above equation, a rice with a 22% (i.e., 22 PA) amylose and a 7 ASV, a Satake Milling Degree of 85, cooked in measured water at a 1.75:1 water:rice ratio has a predicted firmness of 7.9 Pabst Units. A rice with a 26 PA and a 3 ASV, a Satake Milling Degree of 85, cooked in measured water at a 1.75:1 water:rice ratio has a predicted firmness of 8.5 Pabst Units. (The firmness difference associated with 1 Pabst unit is significant in taste testing.) Increasing water/rice ratio softens the rice with higher ratio's required for higher PA and higher ASV rice (i.e., cooked to the equivalent firmness).

Table 8 shows the predicted RVA amylograph viscosities and grain cooking behaviors based on the regression equation shown above. The Table shows a number of useful relationships including that between SI and the water/rice ratio required to achieve a given firmness and between SI and the cooked grain firmness obtained at a given water/rice ratio. FIGS. 6A & 6B show the predicted relationships between grain starch index and cooked grain firmness when the grains are cooked with a water to rice ratio of 1.75 and between RVA amylograph setback viscosity and cooked grain firmness when the grains are cooked with a water to rice ratio of 1.75.

TABLE 8

STARCH INDEX - PASTE AND GRAIN COOKING BEHAVIOR

| SCREENING TEST | | | PASTE AMYLOGRAPH - RVA | | | | COOKED GRAIN | |
|---|---|---|---|---|---|---|---|---|
| SI | PA | ASV | PEAK | HOT | COOL | SETBACK | FIRMNESS[1] | W/R RATIO[2] |
| 17 | 14 | 3 | 485 | 125 | 182 | −303 | 1.7 | 1.30 |
| 21 | 14 | 7 | 438 | 145 | 243 | −195 | 3.3 | 1.45 |
| 21 | 18 | 3 | 433 | 124 | 215 | −217 | 4.0 | 1.52 |
| 25 | 18 | 7 | 385 | 144 | 276 | −109 | 5.6 | 1.67 |
| 25 | 22 | 3 | 380 | 122 | 248 | −132 | 6.3 | 1.73 |

TABLE 8-continued

STARCH INDEX - PASTE AND GRAIN COOKING BEHAVIOR

| SCREENING TEST | | | PASTE AMYLOGRAPH - RVA | | | | COOKED GRAIN | |
|---|---|---|---|---|---|---|---|---|
| SI | PA | ASV | PEAK | HOT | COOL | SETBACK | FIRMNESS[1] | W/R RATIO[2] |
| 29 | 22 | 7 | 333 | 142 | 309 | −23 | 7.9 | 1.88 |
| 29 | 26 | 3 | 327 | 121 | 281 | −46 | 8.5 | 1.95 |
| 33 | 26 | 7 | 280 | 141 | 343 | 63 | 10.1 | 2.10 |
| 33 | 30 | 3 | 275 | 120 | 315 | 40 | 10.8 | 2.17 |

[1]The firmness of cooked rice in Pabst Unit when the rice is cooked with an amount of water that gives a water to rice (W/R) ratio by volume of 1.75.
[2]The volume ratio of water to rice required to cook the grains to a firmness of 7 Pabst Units.

Even though the above relationships were established based on the outcomes of particular amylograph and cooking tests, the basic principles are clear and provide the guidelines and screening tools for breeding a rice line to meet specific cooking behavior and product requirements. For example, the results show that for high ASV (low gelatinization temperature) rice a higher water/rice ratio is required to achieve cooked rice of a given firmness. This indicates a commensurate increase in cooking time for such rice since the time required to absorb the water increases essentially in proportion to the required water/rice ratio.

The amylograph data of the studies presented above was obtained using a Newport Scientific Rapid Visco Analyzer. The grain was milled, ground through a 0.5 mm screen, and mixed into a 12.3% by wt. aqueous paste (3.5 gm/25 gm; rice/water). The test receptacle is held at a temperature of 60° C. for 1 minute, which is then increased to 80° C. over 6 minutes, to 95° C. over 1 minute, held at 95° C. for 4.5 minutes, cooled to 50° C. over 2.5 minutes, then held for 5 minutes at 50° C.

7.5. Application of Starch Index in Screening and Breeding of Desirable Rice Plants An important finding of the regression analysis for cooked grain firmness (see above) is that grains within a particular set of PA, ASV and SI values can all be cooked to the range of firmness of traditional, good quality basmati rice preparations. Table 9 shows the set of values that defines such grains. These values may be advantageously used as selection criteria in breeding programs.

TABLE 9

| | | PERCENT AMYLOSE (PA) | | | | | | |
|---|---|---|---|---|---|---|---|---|
| | | 22 | 23 | 24 | 25 | 26 | 27 | 28 | 29 |
| ASV | 3 | | | 27 | 28 | 29 | 30 | 31 | 32 |
| | 4 | | 27 | 28 | 29 | 30 | 31 | 32 | 33 |
| | 5 | 27 | 28 | 29 | 30 | 31 | 32 | 33 | 34 |
| | 6 | 28 | 29 | 30 | 31 | 32 | 33 | 34 | 35 |
| | 7 | 29 | 30 | 31 | 32 | 33 | 34 | 35 | |
| | | STARCH INDEX | | | | | | | |

Grains with starch property values shown in Table 9, however, will have different amylograph viscosities and require different amounts of water and time to cook to the desired firmness. For example, grains having amylose and ASV combination towards the top left corner of the set (SI≈27 to 30) will tend to have an amylograph with higher peak viscosity, lower cool paste viscosity, a setback below or close to zero, and be faster cooking with less water required to reach the desired firmness. Grains in the center region of the set (SI≈29 to 32) will have a lower amylograph peak viscosity, a higher cool paste viscosity, generally a positive setback, and require more water to cook to the desired firmness. Aged traditional basmati rice from India and Pakistan is generally in this region. Grains towards the lower right hand corner (SI≈31 to 34) will have a low peak viscosity and a high cool paste viscosity and a positive setback. These products will require less aging and can be milled to a higher degree without having the cooked grain be soft and sticky. These grains will take longer to cook but have many of the favorable characteristics of parboiled basmati but with a white color and high aroma and taste, since no parboil processing is involved.

8. EXAMPLE 3: BREEDING OF THE BAS-867 AND RT1117 RICE LINES

Twenty-two basmati lines from the USDA World Germplasm Collection, Beltsville, Md. and thirteen semi-dwarf, long grain lines were selected for the initial crosses, and these are listed in Tables 1 and 2, respectively, along with quality data collected from the original seeds. The basmati seed from the USDA were identified as having come from Pakistan. All were tested as received for aroma, grain length, amylose, ASV, and elongation during cooking. The basmati seeds were increased in greenhouses (RiceTec, Inc., Alvin, Tex.) before use. The semi-dwarf, long grain lines included a number of overseas varieties and covered a range of PA and ASV combinations so that a portfolio of starch properties could be generated.

All of the USDA basmati lines were crossed to select semi-dwarf, long grain line in the greenhouse and the F1's were then topcrossed or backcrossed with the U.S. lines. A number of crosses were discarded in the greenhouse due to very late maturity, being too tall, photoperiod sensitivity, or other undesirable traits. Twenty-three cross combinations and 500 plants were moved into the field at the F2 stage. These combinations included fourteen of the original basmati lines in various combinations with the thirteen semi-dwarf, long grain lines.

The selection criteria used at each stage of the development process are shown in Table 10.

TABLE 10

Selection Process for Development of Basmati Line 17867

| Gen.[1] | Location | Primary Selection Criteria |
|---|---|---|
| F1 | GH | Plant type |
| TC1-F1 | GH | Photoperiod sensitivity[2], height, tiller number and strength, seed set |
| F2 | AL | Photoperiod sensitivity, height, adaptation, aroma, grain size[7], shape, erect plant type |

TABLE 10-continued

Selection Process for Development of Basmati Line 17867

| Gen.[1] | Location | Primary Selection Criteria |
|---|---|---|
| F3 | PR | Adaptation[6], aroma, grain shape, erect plant type |
| F4 | AL | Adaptation, grain shape, phenotypic yield potential |
| F5 | PR | Adaptation, grain length, aroma |
| F6 | AL | Yield, milling[8], grain dimensions[7], starch index, elongation, maturity |
| F7 | PR | selection for plant type, rough rice dimensions, quality |
| F8 | AL | Field adaptations[6], outcrossing tendencies[4], lodging, yield, milling, all quality characters[3] |
| F9 | PR | Increase only, no selection pressure; complete quality assessment |
| F10 | AL | No Selection pressure; complete quality assessment, production suitability[5] |
| F11 | PR | All quality parameters, production suitability, increase |
| F12 | AL | Seed Increase |
| F13 | PR | Seed Increase |
| F14 | AL | Seed Increase |

[1]Generation.
[2]Photoperiod sensitivity is determined by planting in Texas in March through May. If line is photoperiod insensitive it normally will flower 90 to 110 days after planting. In contrast, a photoperiod sensitive line will remain vegetative for a longer period and flower much later in the year.
[3]Quality characteristics include grain and cooking traits as well as grain milling ability.
[4]Outcrossing tendency is measured using a hybrid production field. It can also be selected by examining pollen and anther development and stigma characteristics.
[5]Production stability pertains to the potential for high yields when cultivated using low field production inputs.
[6]Adaptation and field adaptation are the same thing. They are measured by producing a line across a number of different environments or locations within a single year or by producing a line over a number of years.
[7]Grain dimensions are grain length and width and can be determined in the field by manually threshing rough rice and measuring the dehulled grain or by measurements in the laboratory after harvest.
[8]Milling pertains to head grain or whole grain yields.

The average of the original measured properties of the lines at the F2 stage were: (i) percent amylose of 25.2 (range 21.2 to 27.4), (ii) ASV of 5.4 (range 3.8 to 7.0), (iii) grain length of 6.3 mm (range 5.9 to 7.0), and (iv) elongation during cooking of 105% (range 88% to 130%). The 500 F2 plant rows were grown in Texas. As a result of further selection, 1,500 F3 panicle rows were grown in Puerto Rico. This was followed by selecting and growing 6,500 F4 panicle rows in Texas. Plant type, photoperiod sensitivity, grain shape, aroma, and elongation during cooking were primary selection criteria during these early generations.

In generations from F3 through F6, each panicle row was selected for plant height preferred to be from 95–115 cm; plant lodging preferred to be from 0–5%, plant maturity preferred to be from 100–125 days; tillering ability preferred to be from 3–5 tillers per plant; grain dimensions preferred to be 6.5–7.5 mm long and 1.7–1.95 mm wide. In generations from F5 through F10, each candidate was selected for grain yield potential of at least 4,000 lbs per acre; grain elongation during cooking of at least 75%; grain bursting index from 1–3; grain chalkiness in milled rice of less than 15%; aroma levels of 2-AP of greater than 100 ppb; and starch properties of PA from 23.0 to 27.0, and ASV from 3 to 7. The whole grain milling percentage was evaluated from F6 through F12 and had to be at least 40% to be selected and advanced to the next generation.

Plant populations were then moved to the F5 generation (approximately 95% pure) with the primary selection criteria being (i) a field assessment of plant characteristics, including height, tillering, panicle and grain appearance, subjective aroma, and disease tolerance, and (ii) a laboratory assessment of grain dimensions, starch properties, elongation during cooking, and aroma (2-acetyl-1-pyrroline). Approximately 100 field strips of different product candidates, at the F5 stage, were tested for field yield, milling efficiency, amylose content, ASV, cooked grain elongation, aroma and disease tolerance. The candidates were grown in Alvin, Tex. At this stage it became possible to characterize and classify the products and families against the selection criteria.

The F6 and F7 generations, like the F5 generation, were advanced as panicle rows. At each stage, in excess of 10,000 rows were planted, and selections made therein. As seed amounts increased, more data was generated, but most selection pressure was applied for adaptation and plant types expected to perform well in U.S. conditions. In the F7 generation, bulks from F6 plant rows in Alvin (AL) were grown in Puerto Rico (PR), and these bulks were harvested for planting as yield trial plots back in Alvin. At the same time, 939 F7 panicle rows in PR were selected, and planted as 50 foot strips in Alvin, and numbered 17,001 to 17,939. There were many separate selections for each of the crosses shown in Table 11. The average properties of the selections within a cross are shown in this table.

The elongation screening test reported in Table 11 consisted of a 30 minute soak followed by a 12 minute cooking in excess water. It can be seen that the cooked length (and elongation during cooking) tends to be lower with increasing Starch Index. This effect is partly associated with the need to cook high Starch Index rice for longer than 12 minutes to achieve full elongation.

TABLE 11

ADVANCE GENERATION BREEDING LINES

| CROSS | FIELD[1] YIELD | MILLING[2] TOTAL | WHOLE | PA | ASV | SI | ELONG.[3] | 2-AP |
|---|---|---|---|---|---|---|---|---|
| LC2327 | 3,978 | 68 | 34 | 22.5 | 4.2 | 26.7 | 120% | 0 |
| LC2281 | 3,691 | 69 | 42 | 23.1 | 3.7 | 26.8 | 131% | 8 |
| LC2276 | 3,922 | 69 | 44 | 23.0 | 4.1 | 27.1 | 97% | 8 |
| LC2287 | 2,985 | 68 | 40 | 23.7 | 3.5 | 27.2 | 117% | 11 |
| LC2294-A | 3,704 | 71 | 52 | 24.3 | 3.3 | 27.6 | 73% | 10 |
| LC2282 | 5,159 | 70 | 53 | 24.8 | 3.6 | 28.3 | 69% | 12 |
| LC2310 | 3,970 | 70 | 55 | 24.7 | 4.2 | 28.9 | 94% | 10 |

TABLE 11-continued

| | ADVANCE GENERATION BREEDING LINES | | | | | | | |
|---|---|---|---|---|---|---|---|---|
| | FIELD[1] | MILLING[2] | | | | | | |
| CROSS | YIELD | TOTAL | WHOLE | PA | ASV | SI | ELONG.[3] | 2-AP |
| LC2480 | 4,475 | 69 | 46 | 25.1 | 4.2 | 29.3 | 71% | 9 |
| LC2325 | 4,130 | 69 | 52 | 27.1 | 4.1 | 31.2 | 50% | 14 |
| LC2294-B | 5,265 | 67 | 52 | 27.8 | 7.0 | 34.8 | 65% | 9 |

[1]Yields are in units of lbs/acre.
[2]Percent of TOTAL Milling yields or WHOLE Grain yield.
[3]Percent elongation of cooked grain.
[4]2-AP content, the units are 100 parts per billion (ppb).

The testing of rice cooking behavior at the advanced stages of the breeding program included the measurement of the propensity of grains to burst as they elongate. A bursting test was developed consisting of cooking samples to a given firmness, measuring elongation and comparing the grain appearance to a set of ten standards for increasing propensity to burst. Cooking grains to a given firmness is superior (but more time consuming) to the simple thirty minute soak/twelve minute cook screening test for elongation. Samples which differ in starch properties, or age, will cook to a different degree in a fixed time and this can obscure testing for bursting propensity and elongation. The simple screening test is acceptable for early generation testing but not for final product selection.

In general, there was a great similarity between the grain properties of selections within a cross. This is valuable in evaluating crosses and in guiding future crosses and selections. Several of these lines, from five crosses, were selected for seed increases. The selections came from the following crosses:

| |
|---|
| LC2310 = CB801/Bas-433 (PI385455)//CB801E<br>lines: (ID#s 17867, 17258, 17864) |
| LC2281 = CB801/Bas-122 (PI385418)//CB801G<br>line: (ID# 17110) |
| LC2276 = CB801/Bas-(PI392153)//L201<br>lines: (ID#s 17165, 17185, 17186) |
| LC2480 = Bas-397(PI385452)/GPI 130//Leah<br>line: (ID# RT1117) |
| LC2310 = CB801/Bas-433(PI385455)//CB801E<br>line: (ID# BasLgSel) |

Panicle rows of these and other lines were simultaneously advanced to give more uniform seed increase for later production and further product refinement. As a result of the evaluation of the F10 and F11 seed increase and test results, the product ID# 17867, designed Basmati 867 or Bas 867, was increased in the F12 generation.

The plant and grain characteristics of four of the advanced lines—ID# 17867 (Bas-867), RT1117, RT1121 and BasLgSel—are shown in Table 12.

TABLE 12

| | BAS 867 AND RT1117 | | | |
|---|---|---|---|---|
| GRAIN PROPERTIES | BAS 867 | RT1117 | RT1121 | BasLgSel |
| MILLED GRAIN DIMENSIONS | | | | |
| LENGTH/WIDTH | 3.65 | 3.92 | 3.87 | 3.77 |
| WIDTH (mm) | 1.85 | 1.85 | 1.77 | 1.90 |
| LENGTH (mm) | 6.75 | 7.26 | 6.49 | 7.16 |
| CHALK IN MILLED RICE (%) | 8 | 7 | 4 | 4 |
| ELONGATION DURING COOKING (%) | 90 | 75 | 90 | 73 |
| BURSTING DURING COOKING (BURST INDEX) | 2 | 3 | 4 | 4 |
| TASTE AND AROMA 2-AP (ppd) | 360–600 | 150 | 400–450 | 250–300 |
| STARCH PROPERTIES | | | | |
| STARCH INDEX | 29.0 | 29.1 | 28.9 | 30.9 |
| PA | 24.5 | 26.2 | 25.8 | 24.7 |
| ASV | 4.5 | 2.9 | 3.1 | 6.2 |
| PEAK PASTE RVA | 336 | 452 | 405 | 381 |
| HOT PASTE RVA | 131 | 159 | 151 | 122 |
| COOL PASTE RVA | 286 | 320 | 319 | 265 |
| SETBACK RVA | −50 | −132 | −86 | −116 |
| AGRONOMIC PROPERTIES | | | | |
| FIELD YIELD (LBS/ACRE) | 5,300 | 5,400 | 5,000 | 5,300 |
| WHOLE GRAIN MILLING (%) | 50 | 45 | 41 | 42 |
| PLANT HEIGHT (cm) | 119 | 115 | 115 | 120 |
| PLANT LODGING (%) | 0 | 0 | 0 | 0 |
| MATURITY (days) | 128 | 124 | 125 | 125 |

TABLE 12-continued

BAS 867 AND RT1117

| GRAIN PROPERTIES | BAS 867 | RT1117 | RT1121 | BasLgSel |
|---|---|---|---|---|
| TILLERING | 4 | 4 | 4 | 4 |
| DISEASE TOLERANCE | | | | |
| BLAST | MOD. TOL. | MOD. TOL. | MOD. TOL. | MOD. TOL. |
| STRAIGHTHEAD | SUSCEPL. | MOD. SUC. | SUSCEPL. | SUSCEPL. |
| SHEATHBLIGHT | MOD. TOL. | MOD. TOL. | MOD. TOL. | MOD. TOL. |

EXAMPLE 4: THE PLANT AND GRAIN CHARACTERISTICS OF BAS-867 RICE LINE

9.1. Field and Milling Performance

FIGS. 7 and 8 show the results of regional trials covering Texas and Arkansas. Each point on the graph represents one trial location.

FIG. 7 shows Basmati 867 field yield relative to a commercial specialty variety RTA 1002, and commodity varieties RT7015, Lemont and Cypress. The placement of many RTA 1002 points to the right of the diagonal line show that Basmati 867 has a field yield of about 1,000 lbs/acre higher than the specialty variety. The points to the left of the diagonal line show that Basmati 867 has a field yield about 500 lbs/acre below the commodity rice tested. The average field yield of Bas 867 in over 22 individual tests in two different years was 5,280 lbs/acre. These results are twice as high as traditional basmati rice grown in India and Pakistan.

FIG. 8 shows that Basmati 867 has about a ten point lower Whole Grain Index than the commodity and specialty rice variety shown. The average milling yield over 12 tests in two years, where milling efficiency was measured, was 44/68 (Whole/Total). These results are similar to those for traditional basmati grown in India and Pakistan.

Disease screening of Basmati 867 showed moderate susceptibility to blast, slightly better tolerance to blast and sheath-blight than the commercial specialty rice, and a similar high susceptibility to straighthead. Varieties susceptible to straighthead should be grown on heavy soil and this physiological disorder is controlled with water management techniques. The disease tolerance of Basmati 867 is satisfactory.

The Basmati 867 plant height is approximately 119 cm as compared to 89 cm for Lemont and 101 cm for RT7015. Days to maturity of Basmati 867 is 128 days as compared to 120 days for Lemont and 110 days for RT7015. The leaf blade of the Basmati 867 plant is very dark green, erect, narrow and smooth with a well exerted panicle. The plant is resistant to lodging due to its sturdy stem and generally open leaf structure. The plant has a high tillering ability and fair to good seedling vigor.

9.2. Grain Characteristics

Table 13 shows the typical grain properties of Basmati 867 grown in the United States. The comparative data for traditional Indian basmati is the average of the properties shown in Table 1. The Basmati 867 grain was assayed approximately one year after harvesting and is about one year "younger" than the Indian basmati rice assayed. The milling degree data for the Basmati 867 are the test results for the samples which were tested on the RVA amylograph and can be modified by the choice of milling process.

TABLE 13

COMPARISON OF BASMATI 867 AND INDIAN BASMATI RICE

| | BASMATI 867 HARVEST TIME | | | INDIAN BASMATI |
|---|---|---|---|---|
| | FLORIDA 1ST CROP JUNE | FLORIDA 2ND CROP JULY | TEXAS 1ST CROP NOVEMBER | AVERAGE OF FOUR BRANDS |
| PA | 23.9 | 23.7 | 24.3 | 23.0 |
| ASV | 4.7 | 4.8 | 5.0 | 6.6 |
| STARCH INDEX | 28.6 | 28.5 | 29.3 | 29.6 |
| LENGTH | 6.61 | 6.62 | 6.82 | 7.33 |
| WIDTH | 1.85 | 1.87 | 1.99 | 1.78 |
| LENGTH/WIDTH | 3.57 | 3.54 | 3.44 | 4.12 |
| ELONGATION | 86% | 93% | 98% | 102% |
| MILLING DEGREE (SMD) | 85 | 66 | 94 | 85 |
| WHITENESS | 37.5 | 34.6 | 39.9 | 38.3 |
| TRANSPARENCY | 2.8 | 1.6 | 2.8 | 2.2 |
| PEAK | 363 | 315 | 331 | 319 |
| HOT | 134 | 132 | 126 | 169 |
| COOL | 280 | 288 | 290 | 375 |
| SETBACK | −83 | −27 | −41 | 56 |

The Starch Index and the Setback of Basmati 867 indicates that the rice is slightly softer cooking at a given water/rice ratio and degree of milling than the average of the Indian products shown. The difference in Setback is somewhat more than might be expected from the difference in Starch Index, possibly due to the aging of the Indian products.

A comparison of the amylograph of Basmati 867 and a traditional basmati was made at various different paste concentrations. This is shown in Table 14. The data show that Basmati 867 requires an increase in paste concentration (lower water/rice ratio) of about 1% point to have a similar hot and cool paste viscosity as the Indian basmati.

TABLE 14

EFFECT OF PASTE CONCENTRATION ON
BASMATI 867 AND INDIAN BASMATI AMYLOGRAPHS

| PASTE | | PEAK | HOT | COOL | SETBACK |
|---|---|---|---|---|---|
| 11% | INDIAN | 216 | 136 | 307 | 91 |
|  | B-867 | 202 | 96 | 235 | 33 |
| 12% | INDIAN | 431 | 196 | 420 | -11 |
|  | B-867 | 361 | 148 | 337 | -33 |
| 13% | INDIAN | 575 | 221 | 479 | -96 |
|  | B-867 | 458 | 174 | 387 | -71 |

In addition to changes in water/rice ratio and aging, the cooking behavior and cooked product attributes of Basmati 867 can be modified by the methods and procedures described in U.S. Pat. No. 5,208,063 (Milling Process for Controlling Rice Cooking Characteristics).

The uncooked grain dimensions of Basmati 867 show the product to be not quite as slender as the average of the Indian products shown in Table 1. Elongation during cooking and cooked grain appearance is essentially the same. Cooked grain appearance and amylograph properties of Basmati 867 were compared with a data bank of basmati and other rice products by Flour Milling and Baking Research Association (FMBRA) in the United Kingdom.

Samples of Basmati 867 together with samples of Indian and Pakistan basmati rice were blind tested by FMBRA using the basmati authenticity tests developed for cooked grain dimensions and starch characteristics. Basmati 867 passed these authenticity tests as indicated in FIGS. 9 and 10.

Basmati 867 has significantly less chalk (white center and white belly) than traditional basmati products and the grains are more translucent. This data is presented Table 15.

TABLE 15

| TYPICAL LEVELS OF CHALKY AND DISCOLORED GRAINS | | |
|---|---|---|
|  | % CHALKY | % DISCOLORED |
| INDIAN BRAND A | 28.1 | 13.9 |
| INDIAN BRAND B | 32.5 | 10.0 |
| INDIAN BRAND C | 22.9 | 26.4 |
| BASMATI 867 | 8.1 | 3.4 |

The level of 2-acetyl-1-pyrroline (the taste and aroma compound) in Basmati 867 is significantly higher than that in Indian basmati and in Texmati® (the non-elongating American basmati type rice currently grown and marketed in the U.S.). This is shown in Table 16.

TABLE 16

| LEVEL OF 2-AP IN VARIOUS RICE PRODUCTS | |
|---|---|
|  | ppb |
| INDIAN BASMATI BRANDS | |
| PARI | 89 |
| TILDA | 185 |
| SAINSBURY | 208 |
| TEXMATI ® BRAND | 181 |
| ASMATI 867 | SAMPLE NO. |
| 1 | 238 |
| 2 | 473 |
| 3 | 483 |
| 4 | 445 |
| 5 | 520 |

The second crop shown in Table 13 was produced as a ratoon crop in Florida. The ratoon crop product contained more hulls and bran per unit weight of white grain and the product tested was of a low milling degree. A higher milling degree was achieved from second crop basmati by milling for a longer time or by using more severe conditions. The ability to produce a second crop from a single planting of seed is of significant economic advantage and can only be achieved from a medium to short maturity plant such as Basmati 867. The photosensitive long maturing traditional basmati plants can not be second cropped commercially.

9.3. Consumer Evaluations

The laboratory data comparing the properties and relative performance of Basmati 867 and traditional basmati rice was corroborated by extensive consumer testing. An independent market research company, Research Services of Great Britain (RSGB), conducted all the tests, including the random purchase of the Indian basmati rice used and selection of participants. The test participants were all frequent basmati consumers in the UK. Comparisons were made with a leading producers brand Test Series 1) and a leading store brand Test Series 2). The tests included comparisons of Basmati 867 products milled to different specifications and the use of different cooking methods.

9.3.1. Test Series 1

In this test, Basmati 867 was compared with a leading producers brand of Indian basmati rice. The products were provided in unmarked pairs to the 44 participants for comparison. Products were compared uncooked and cooked. Products were cooked by RSGB personnel using the traditional Indian presoaking and measured water technique in automatic electric rice cookers. Participants were not aware of the origin of the samples and the test was replicated randomly with each participant comparing the same set of samples twice.

TABLE 17

BASMATI 867 AND AN INDIAN PRODUCERS BRAND:
COMPARISON OF UNCOOKED RICE ATTRIBUTES

| | Percent of Participants Selecting | | |
|---|---|---|---|
|  | B-867 | INDIAN | NEITHER |
| RICE WITH MOST AROMA | 52 | 47 | 1 |
| RICE PREFERRED FOR AROMA | 72 | 27 | 1 |

TABLE 17-continued

BASMATI 867 AND AN INDIAN PRODUCERS BRAND: COMPARISON OF UNCOOKED RICE ATTRIBUTES

|  | Percent of Participants Selecting | | |
|---|---|---|---|
|  | B-867 | INDIAN | NEITHER |
| RICE PREFERRED FOR APPEARANCE | 55 | 45 | 0 |
| RICE PREFERRED OVERALL-UNCOOKED | 66 | 33 | 1 |
| SATAKE MILLING DEGREE | 65 | 102 | |
| WHITENESS | 36 | 41 | |
| TRANSPARENCY | 2.4 | 3.3 | |

Table 17 shows that Basmati 867 was clearly preferred in the uncooked rice comparison. The lower level of chalk and the aroma of Basmati 867 appeared to be significant factors. Table 18 shows that the preferred whiter appearance (due to the higher milling degree) of the Indian rice became more of a factor in the cooked rice comparison. However, the two products were equally preferred overall. Not only were the products equally preferred but of the half who preferred each product on the first test, one half switched preference to the other product on the second (replicate) test. In other words the preference was not associated with a particular group of people and each person had difficulty in deciding which product they preferred.

TABLE 18

BASMATI 867 AND AN INDIAN PRODUCERS BRAND: COMPARISON OF COOKED RICE ATTRIBUTES

|  | Percent of Participants Selecting | | |
|---|---|---|---|
|  | B-867 | INDIAN | NEITHER |
| RICE WITH MOST AROMA | 41 | 58 | 1 |
| RICE PREFERRED FOR AROMA | 59 | 39 | 2 |
| RICE WITH MOST TASTE | 49 | 50 | 1 |
| RICE PREFERRED FOR TASTE | 51 | 49 | 0 |
| RICE PREFERRED FOR APPEARANCE & TEXTURE | 50 | 49 | 1 |
| RICE WHICH IS WHITEST | 13 | 85 | 2 |
| RICE PREFERRED FOR WHITENESS | 33 | 61 | 6 |
| RICE PREFERRED OVERALL | 49 | 51 | |

The Basmati 867 used for Test 1 was milled to a fairly low degree to improve cooked rice texture since the starch properties indicate that Basmati 867 is a somewhat softer cooking rice. This change gives a less preferred whiteness of the cooked rice. It is therefore necessary to strike a balance between whiteness and softness in commercial products.

9.3.2. Test Series 2

In this test Basmati 867 was compared with a leading store brand of Indian Basmati. The products were provided to 449 participants who normally shopped at the store where the basmati store brand was sold. All were frequent basmati consumers. Products were compared at home by the participants. The trials were managed by RSGB. Participants were not aware of the origin of the samples and the tests involved excess water and measured water coloring both of which are used to a similar extent by basmati consumers in the UK.

TABLE 19

BASMATI 867 AND STORE BRAND INDIAN BASMATI: COMPARISON OF COOKED RICE ATTRIBUTES AND OVERALL PREFERENCE

|  | Percentage of Participants Selecting | | |
|---|---|---|---|
|  | B-867 | INDIAN | NEITHER |
| UNCOOKED APPEARANCE | 43 | 18 | 39 |
| AROMA WHILE COOKING | 31 | 28 | 42 |
| COOKED RICE WHITENESS | 46 | 22 | 33 |
| TASTE | 39 | 37 | 24 |
| COOKED RICE TEXTURE | 33 | 43 | 24 |
| RICE PREFERRED OVERALL | 42 | 40 | 18 |
| SATAKE MILLING DEGREE | 96 | 68 | |
| WHITENESS | 40 | 35 | |
| TRANSPARENCY | 3.2 | 1.2 | |

The tests also involved evaluation of the effect of water/rice ratio and the degree of milling of the Basmati 867. Table 19 shows the results of one of the trials in which the store brand Indian basmati was compared by 114 participants with Basmati 867 milled to a 96 Satake Milling Degree. The Basmati 867 used in this test was the first crop product from Florida shown in Table 13 which had been harvested only eight months before the consumer test. The store brand Indian basmati was estimated to have been fifteen months of age. Similar aging of Basmati 867 would have improved the preference scores for texture. In this case the rice was milled to a higher degree than the Indian Basmati which was the reverse of Test Series 1. The effect of the higher degree of milling was evident in the preference scores for cooked rice whiteness. The softer texture of the Basmati 867 was a disadvantage but Basmati 867 and the store brand Indian basmati were equally preferred overall.

The laboratory and consumer testing shows that Basmati 867 is equivalent to traditional good quality Indian and Pakistan basmati and the objective of producing such basmati rice outside of the tractional basmati growing areas has been accomplished according to this invention. Additionally, the invention provides novel rice lines that can be produced with basmati grain properties suited to those who prefer a softer or firmer rice to that of traditional basmati rice and even rice with cooking properties similar in many ways to parboiled basmati rice but without the need to parboil thus preventing the loss of aroma and taste.

10. Deposit of Seeds

On Oct. 31, 1994, seeds of rice lines RT1171, RT11121 and BAS 867 were deposited with the American Type Culture Collection (ATCC), 12301 Parklawn Drive, Rockville, Md. 20852 in compliance with the Budapest Treaty on the International Recognition of the Deposits of Microorganisms for the Purposes of Patent Procedure. The seed deposits were assigned the following accession numbers:

| RICE LINE | ACCESSION NUMBER |
|---|---|
| RT1171 | ATCC 75939 |
| RT1121 | ATCC 75940 |
| BAS 867 | ATCC 75941 |

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosure of which are incorporated by reference in their entireties.

What is claimed is:

1. A rice plant, which plant when cultivated in North, Central or South America, or Caribbean Islands
   a) has a mature height of about 80 cm to about 140 cm;
   b) is substantially photoperiod insensitive; and
   c) produces rice grains having
      i) an average starch index of about 27 to about 35,
      ii) an average 2-acetyl-1-pyrroline content of about 150 ppb to about 2,000 ppb,
      iii) an average length of about 6.2 mm to about 8.0 mm, an average width of about 1.6 mm to about 1.9 mm, and an average length to width ratio of about 3.5 to about 4.5,
      iv) an average of about 41% to about 67% whole grains, and
      v) an average lengthwise increase of about 75% to about 150% when cooked.

2. The rice plant of claim 1, wherein said starch index of i) consists of the sum of percent amylose of about 24 to about 29 and of alkali spreading value of about 2.9 to about 7.

3. The rice plant of claim 2, wherein said rice grains additionally have an average burst index of about 4 to about 1.

4. The rice plant of claim 2, wherein said rice grains consist of less than about 20% chalky, white belly or white center grains.

5. The rice plant of claim 1, wherein said plant produces about 3,000 lbs to about 10,000 lbs of seed per acre.

6. The rice plant of claim 1, which plant
   a) has a mature height of about 119 cm; and
   b) produces rice grains having
      i) an average starch index of about 29, an average percent amylose of about 24.5, and an average alkali spreading value of about 4.5,
      ii) an average 2-acetyl-1-pyrroline content of about 400 ppb,
      iii) an average length of about 6.75 mm, an average width of about 1.85 mm, and an average length to width ratio of about 3.65,
      iv) an average of about 50% whole grains, and
      v) an average lengthwise increase of about 90% when cooked.

7. The rice plant of claim 1, which plant
   a) has a mature height of about 115 cm; and
   b) produces rice grains having
      i) an average starch index of about 29, an average percent amylose of about 26.2, and an average alkali spreading value of about 2.9,
      ii) an average 2-acetyl-1-pyrroline content of about 150 ppb,
      iii) an average length of about 7.26 mm, an average width of about 1.85 mm, and an average length to width ratio of about 3.92,
      iv) an average of about 45% whole grains, and
      v) an average lengthwise increase of about 75% when cooked.

8. A rice plant produced from Bas 867 seed having the accession number ATCC 75941.

9. A rice plant produced from RT1117 seed having the accession number ATCC 75939.

10. The rice plant of claim 1, which plant
    a) has a mature height of about 115 cm; and
    b) produces rice grains having
       i) an average starch index of about 28.9, and average percent amylose of about 25.8, and an average alkali spreading value of about 3.1,
       ii) an average 2-acetyl-1-pyrroline content of about 400 to about 450 ppb,
       iii) an average length of about 6.49 mm, an average width of about 1.77 mm, and an average length to width ratio of about 3.87,
       iv) an average of about 41% whole grains, and
       v) an average lengthwise increase of about 90% when cooked.

11. A rice plant produced from RT1121 seed having the accession number ATCC 75940.

12. A seed produced by the rice plant of any of claims 1 to 11.

13. A rice grain derived from the seed of claim 12.

14. A progeny plant of the rice plant of any of claims 1 to 11.

15. A rice grain, which has
    i) a starch index of about 27 to about 35,
    ii) a 2-acetyl-1-pyrroline content of about 150 ppb to about 2,000 ppb,
    iii) a length of about 6.2 mm to about 8.0 mm, a width of about 1.6 mm to about 1.9 mm, and a length to width ratio of about 3.5 to about 4.5,
    iv) a whole grain index of about 41 to about 63,
    v) a lengthwise increase of about 75% to about 150% when cooked, and
    v) a chalk index of less than about 20.

16. The rice grain of claim 15, which has a 2-acetyl-1-pyrroline content of about 350 ppb to about 600 ppb.

17. The rice grain of claim 15, which has a burst index of about 4 to about 1.

18. A method of selecting a rice plant for breeding or propagation, comprising the steps of:
    a) preparing rice grains from rice seeds;
    b) determining
       i) the percent amylose (PA), and
       ii) the alkali spreading value (ASV) of samples of said grains;
    c) summing said PA and said ASV to obtain the starch index (SI) of said grains;
    d) identifying a rice plant which produces grains having an average PA of about 22 to about 29, an average ASV of about 2.9 to about 7, and an average SI of about 27 to about 35;
    e) selecting a seed from said plant; and
    f) growing said seed into a plant.

19. A method of selecting a rice plant for breeding or propagation, comprising the steps of:
    a) preparing rice grains from rice seeds;
    b) determining
       i) the percent amylose (PA), and
       ii) the alkali spreading value (ASV) of samples of said grains;

c) summing said PA and said ASV to obtain the starch index (SI) of said grains;

d) cooking a sample of said grains and determining the percent elongation of cooked grains;

e) identifying a rice plant which produces grains having an average PA of about 22 to about 29, an average ASV of about 2.9 to about 7, an average SI of about 27 to about 35, and an average cooked grain elongation of about 75% to about 150%;

f) selecting a seed from said plant; and g) growing said seed into a plant.

20. A method of selecting a rice plant for breeding or propagation, comprising the steps of:

a) preparing rice grains from rice seeds;

b) determining i) the percent amylose (PA), and ii) the alkali spreading value (ASV) of samples of said grains;

c) summing said PA and said ASV to obtain the starch index (SI) of said grains;

d) determining the burst index of a sample of said grains;

e) identifying a rice plant which produces grains having an average PA of about 22 to about 29, an average ASV of about 2.9 to about 7, an average SI of about 27 to about 35, and an average burst index of about 4 to about 1;

f) selecting a seed from said plant; and g) growing said seed into a plant.

* * * * *

(12) REEXAMINATION CERTIFICATE (4525th)
United States Patent
Sarreal et al.

(10) Number: US 5,663,484 C1
(45) Certificate Issued: Jan. 29, 2002

(54) RICE LINES BAS 867, RT1117, AND RT112

(75) Inventors: Eugenio S. Sarreal, Pearland; John A. Mann, Friendswood; James Edward Stroike, League City; Robin D. Andrews, Seabrook, all of TX (US)

(73) Assignee: Ricetec, Inc., Alvin, TX (US)

Reexamination Request:
No. 90/005,709, Apr. 28, 2000

Reexamination Certificate for:
Patent No.: 5,663,484
Issued: Sep. 2, 1997
Appl. No.: 08/272,353
Filed: Jul. 8, 1994

(51) Int. Cl.⁷ .............................. A01H 5/00; A01H 5/10
(52) U.S. Cl. ................................... 800/320.2
(58) Field of Search ........................... 47/58.1, DIG. 1; 800/260, 263, 320.2

(56) References Cited

PUBLICATIONS

GRIN Accession No. PI 385455, Feb. 1974.*
GRIN Accession No. PI 385439, Feb. 1974.*
GRIN Accession No. PI 385452, Feb. 1974.*
Chang, T. T. et al., "The Morphology And Varietal Characteristics Of The Rice Plant", *Technical Bulletin*, pp. 17–25 (Dec. 1965).
"Descriptors For Rice Oryza Sativa L.", *International Rice Research Institute and International Board for Plant Genetic Resources,* 6 pages (1980).

"High Yielding Basmati Rice—Problems, Progress And Prospects", *IARI Bulletin,* 48 pages (1980).

"Rice Research In India", Indian Council of Agricultural Research, New Delhi, 6 pages (Oct. 1985).

Little, R.R. et al. "Differential Effect Of Dilute Alkali On 25 Varieties Of Milled White Rice" pp. 111–126 (Mar. 1958).

* cited by examiner

*Primary Examiner*—Amy J. Nelson

(57) ABSTRACT

The invention relates to novel rice lines, *Bas 867, RT1117, and RT1121,* and to plants and grains of these lines [and to a method for breeding these lines. The invention also relates to a novel means for determining the cooking and starch properties of rice grains and its use in identifying desirable rice lines. Specifically, one aspect of the invention relates to]. *The* novel rice lines [whose plants] are semi-dwarf in stature, substantially photoperiod insensitive and high yielding, and produce rice grains having characteristics similar or superior to those of good quality basmati rice. Another aspect of the invention relates to novel rice grains produced from *the* novel rice lines. [The invention provides a method for breeding these novel lines. A third aspect of the invention relates to the finding that the "starch index" (SI) of a rice grain can predict the grain's cooking and starch properties, to a method based thereon for identifying grains that can be cooked to the firmness of traditional basmati rice preparations, and to the use of this method in selecting desirable segregants in rice breeding programs.]

Figure 1B:
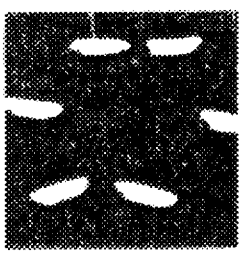
Figure 1B:
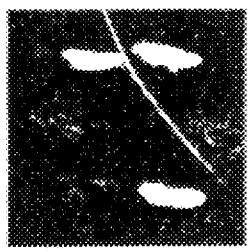
Figure 1D:
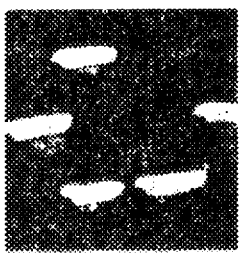
Figure 1D:
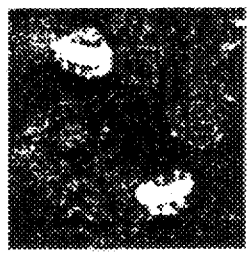
Figure 1F:
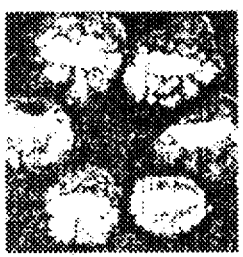
Figure 1F:
Figure 1I:
Figure 1I:
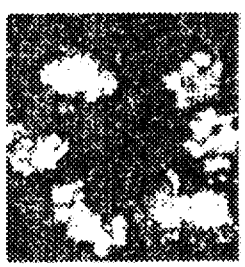
Figure 1I:
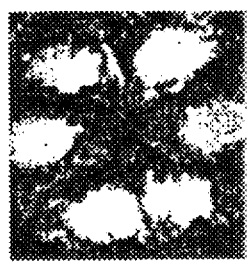
Figure 1K:
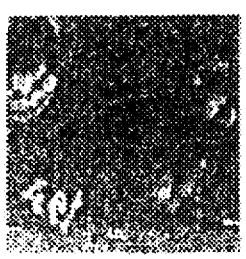
Figure 1K:
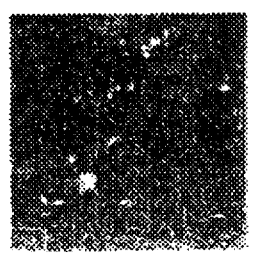
Figure 3A:
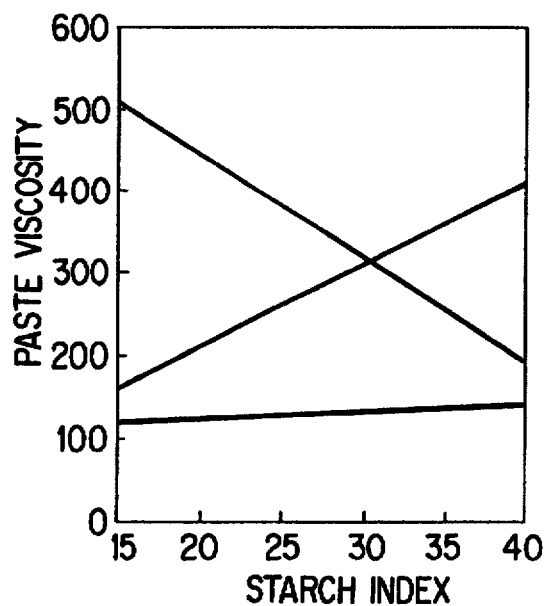
Figure 3B:
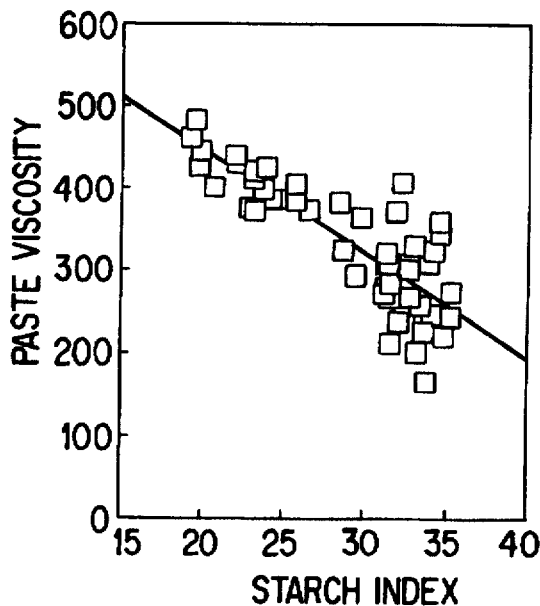
Figure 3C:
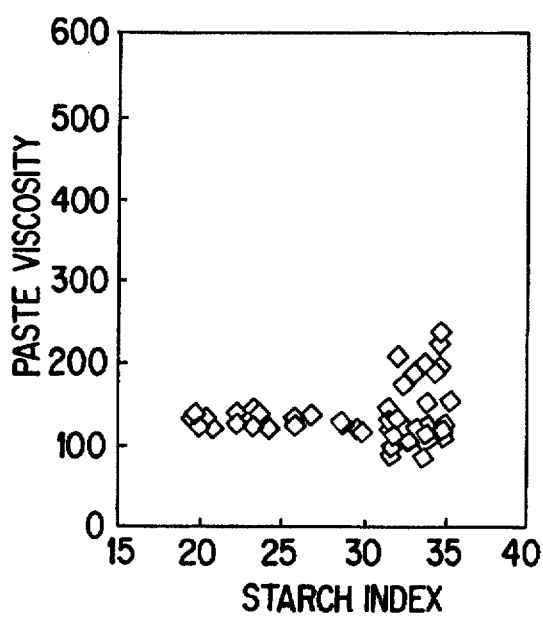
Figure 3D:
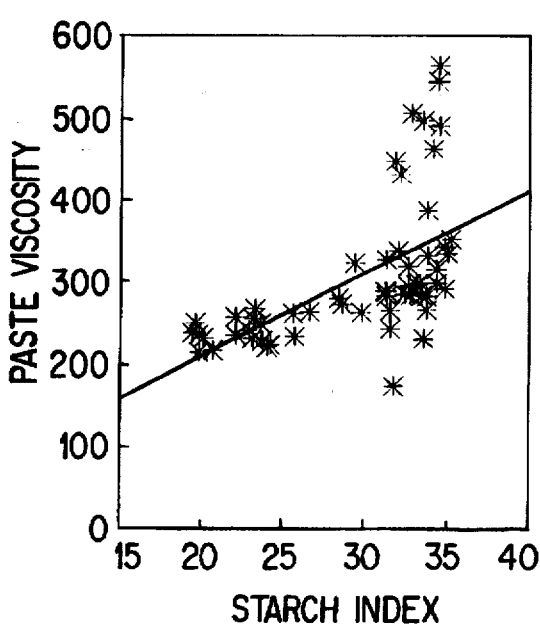
Figure 4:
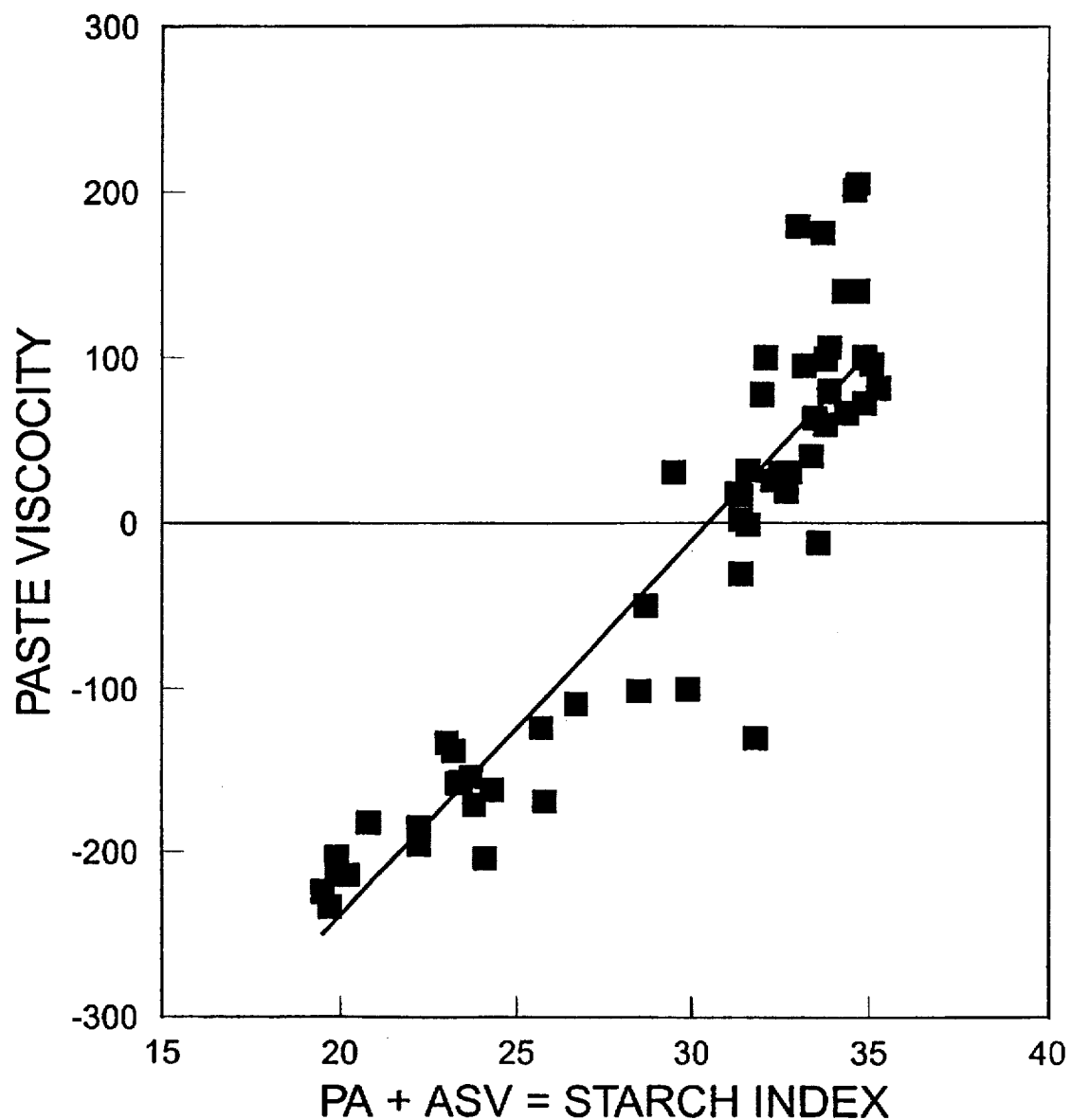
Figure 5:
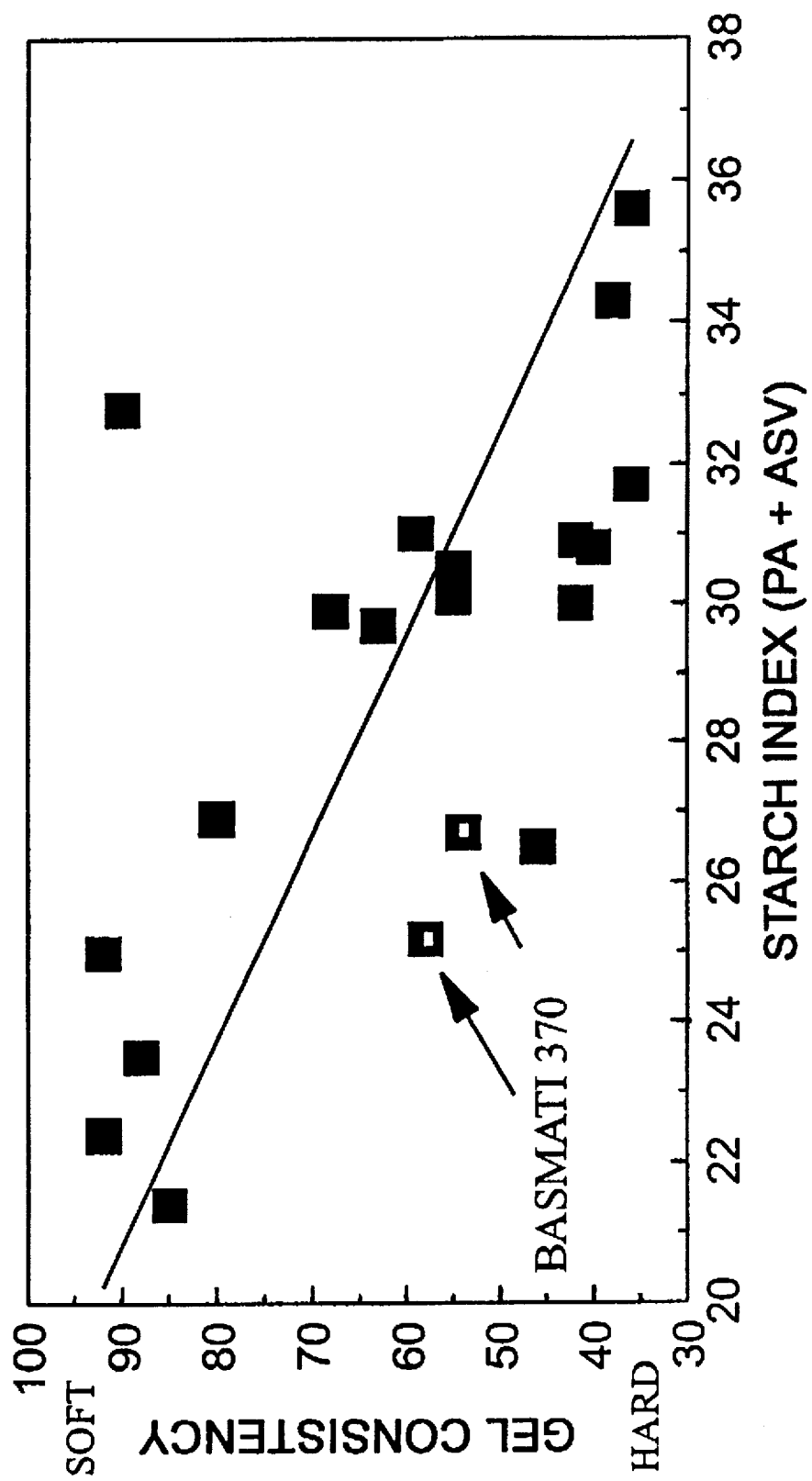
Figure 7:
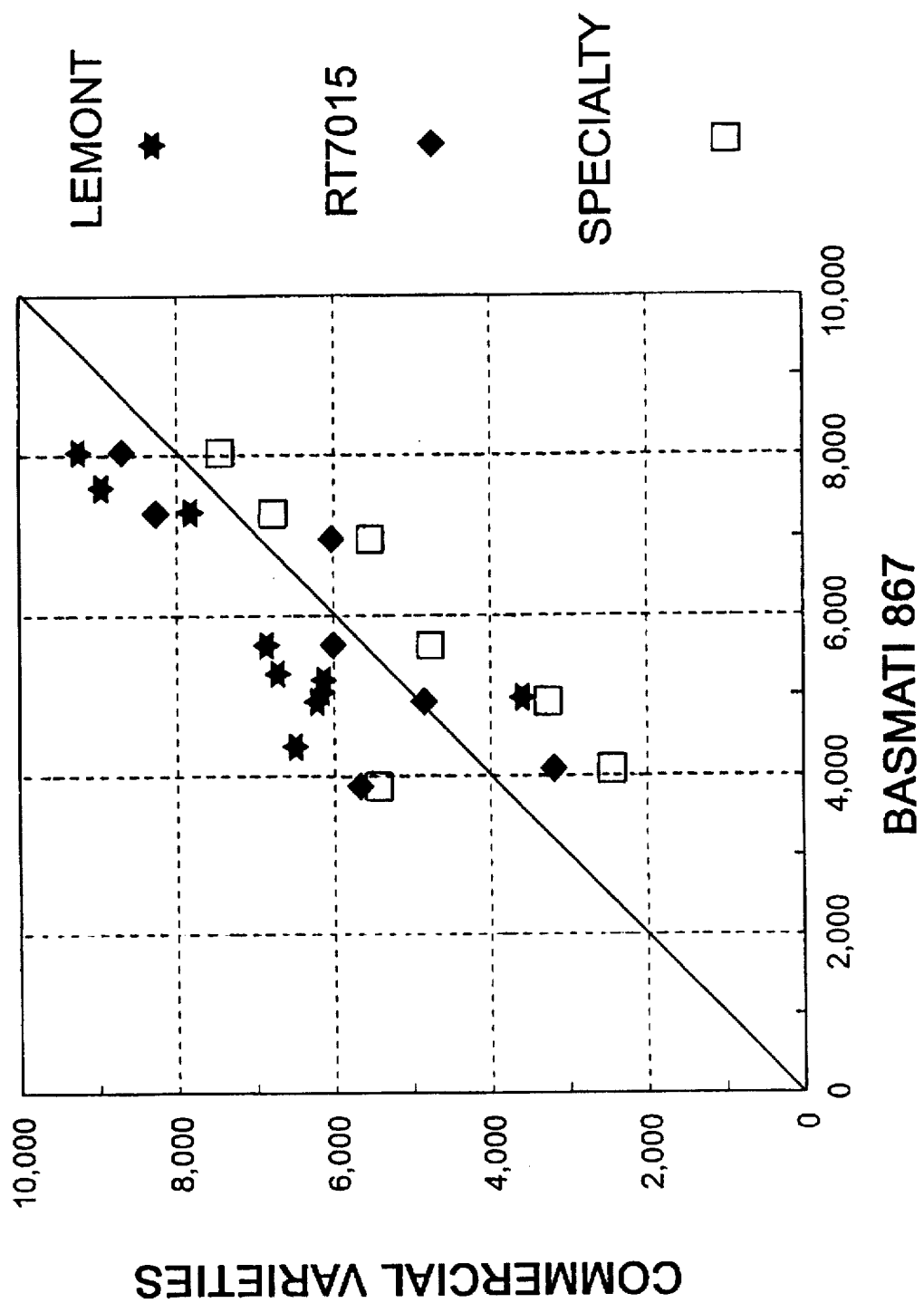
Figure 8:
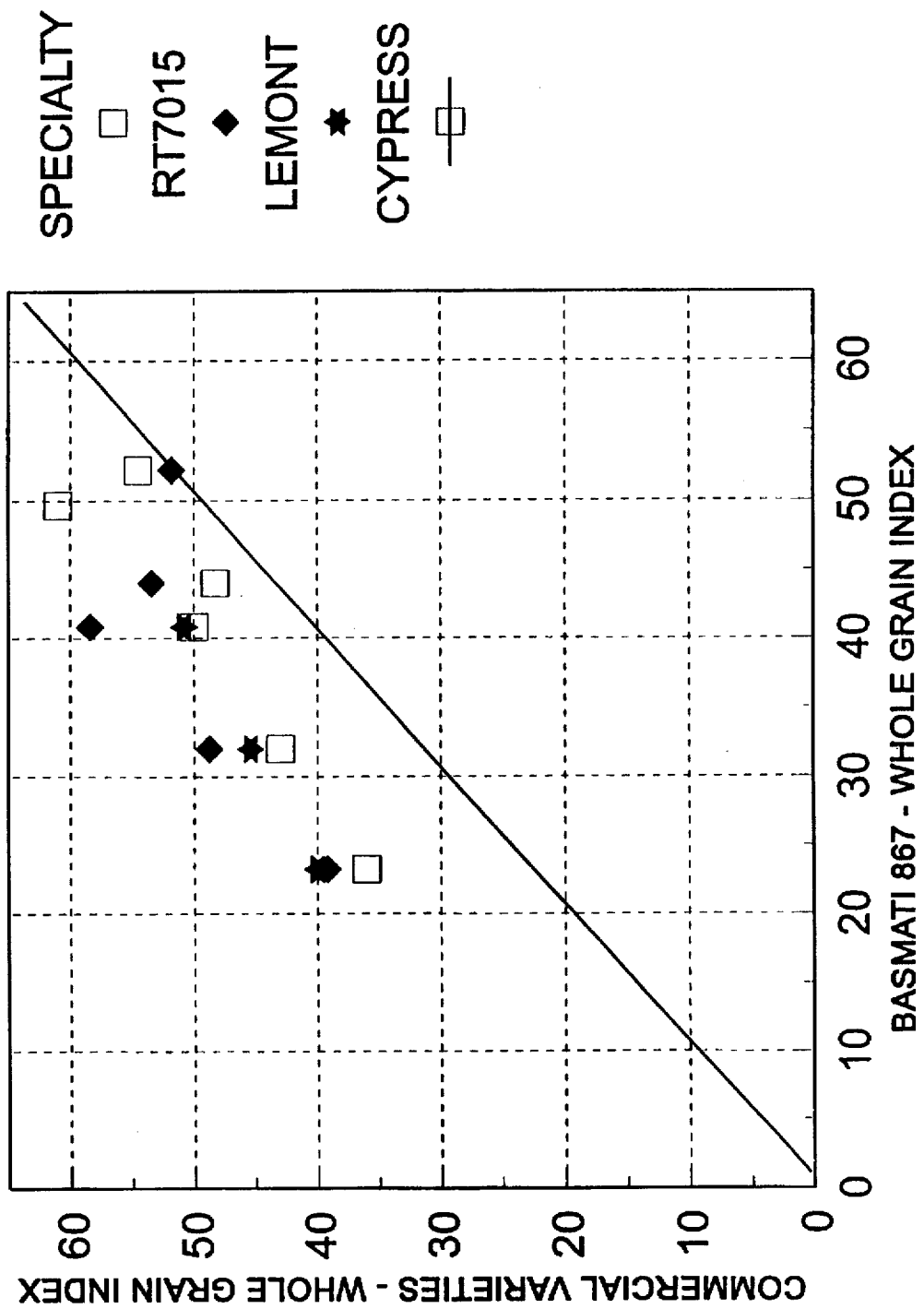
Figure 9:
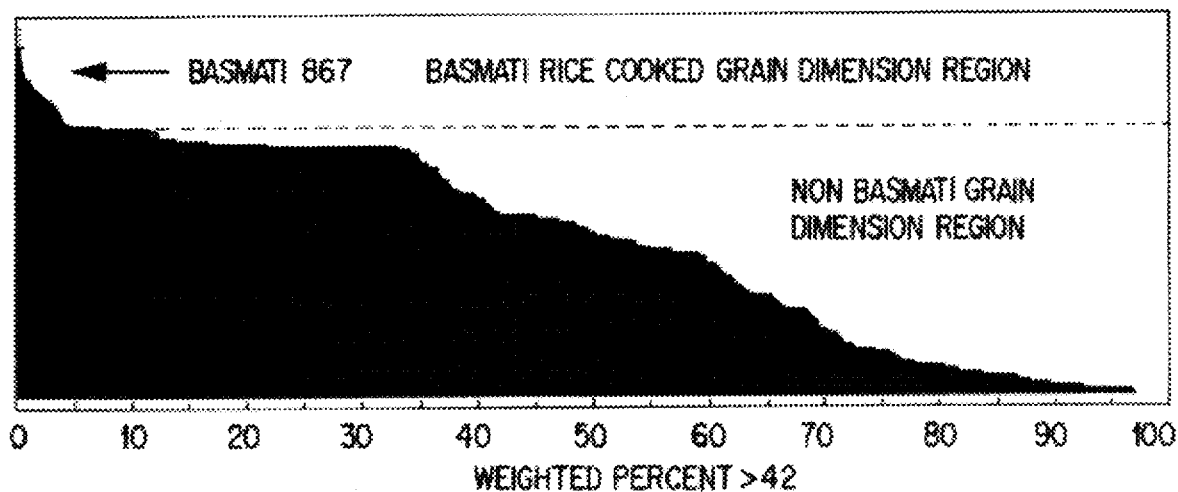

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 22, line 11:

[5 5.4.10. Chalk Index Determination]

Column 22, lines 13–23:
[The chalkiness of a grain sample may be determined as follows:
1. Select whole grains from a sample and place approximately ten grams of whole grains on a light box.
2. Visually identify grains with 50% or more chalk content (can be white belly or white centers) according to standard (see FIGS. 2A–2F) These are scored chalky as grains and separated from the other grains.
3. Weigh chalky grains and calculate the percent chalkiness of sample by weight.]

Column 22, lines 26–27:

5.4.[11]*10*. Starch Index and Its Use in Predicting Cooked Grain Firmness

Column 37, lines 48–50:

[Basmati 867 has significantly less chalk (white center and white belly) than traditional basmati products and the grains are more translucent. This data is presented Table 15.]

Column 37, lines 52–61:

[TABLE 15

TYPICAL LEVELS OF CHALKY AND DISCOLORED GRAINS

|  | % CHALKY | % DISCOLORED |
|---|---|---|
| INDIAN BRAND A | 28.1 | 13.9 |
| INDIAN BRAND B | 32.5 | 10.0 |
| INDIAN BRAND C | 22.9 | 26.4 |
| BASMATI 867 | 8.1 | 3.4] |

AS A RESULT OF REEXAMINATION, IT HAS BEEN DETERMINED THAT:

The patentability of claims 8, 9 and 11 is confirmed.

Claims 1–7, 10 and 14–20 are cancelled.

Claims 12 and 13 are determined to be patentable as amended.

12. A seed produced by the rice plant of any of claims [1 to 11] *8, 9 and 11*.

13. A rice grain [derived] from the seed of [claim] *Claim* 12.

* * * * *